(12) United States Patent
Bray et al.

(10) Patent No.: US 10,964,411 B2
(45) Date of Patent: *Mar. 30, 2021

(54) METHOD FOR QUANTITATIVE ANALYSIS OF COMPLEX PROTEOMIC DATA

(71) Applicants: Tyler Stuart Bray, Chicago, IL (US); Juliesta Elaine Sylvester, Chicago, IL (US); Stephen Joseph Kron, Oak Park, IL (US)

(72) Inventors: Tyler Stuart Bray, Chicago, IL (US); Juliesta Elaine Sylvester, Chicago, IL (US); Stephen Joseph Kron, Oak Park, IL (US)

(*) Notice: Subject to any disclaimer, the term of this patent is extended or adjusted under 35 U.S.C. 154(b) by 829 days.

This patent is subject to a terminal disclaimer.

(21) Appl. No.: 15/487,723

(22) Filed: Apr. 14, 2017

(65) Prior Publication Data
US 2017/0344700 A1 Nov. 30, 2017

Related U.S. Application Data

(63) Continuation of application No. 13/068,026, filed on May 2, 2011, now Pat. No. 9,659,146.

(51) Int. Cl.
*G16B 40/00* (2019.01)
*G01N 33/68* (2006.01)

(52) U.S. Cl.
CPC ......... *G16B 40/00* (2019.02); *G01N 33/6848* (2013.01); *G01N 2570/00* (2013.01)

(58) Field of Classification Search
None
See application file for complete search history.

(56) References Cited

U.S. PATENT DOCUMENTS

| | | |
|---|---|---|
| 6,906,320 B2 | 6/2005 | Sachs et al. |
| 7,026,167 B2 | 4/2006 | Hunt et al. |
| 7,544,518 B2 | 6/2009 | Abersold et al. |
| 7,691,643 B2 | 4/2010 | Yamashita et al. |
| 2005/0048564 A1 | 3/2005 | Emili et al. |
| 2006/0160070 A1 | 7/2006 | Mallal et al. |
| 2007/0016612 A1 | 1/2007 | James et al. |
| 2008/0221802 A1 | 9/2008 | Oda et al. |
| 2012/0283954 A1 | 11/2012 | Bray |

OTHER PUBLICATIONS

Tabb, D. L., et al, (2010). "Repeatability and Reproducibility in Proteomic identifications by Liquid Chrom.-Tandem Mass Spectrometry" J. of Proteome Research 9(2)161-776.
Maccoss, M. 1., et al (2002). "Probability-Based validation of Protein Identifications Using a Modified SEQUEST Algorithm." Anal Chem 74(21): 5593-5599.
Sharan, R., et al (2007), "Network-based prediction of protein function," Molecular Systems Biology 3(88)1-12.
Xu, C. and Bin Ma (2006). "Software for computational peptide identification from MS-MS data,"Drug Discovery Today 11(13/14): 595-600.
Cox, J. and M. Mann (2007). "Is Proteomics the New Genomics?" Cell 130 1(3): 395-398.
Joyce, A. R. and B. O. Palsson (2006). "The model organism as a system: integrating 'omics' data sets." Molecular Cell Biology 6: 199-210.
Coon, J.J., et al. (2005), "Tandem Mass Spectrometry for Peptide Protein Sequence Analysis."Biotechniques 38 (4) 519-523.
Deutsch, E.W., et al.(2008). Data analysis and bioinformatics tools for tandem mass spectrometry in proteomics, Physiol Genomics 33: 18-25.
Ekins, S., J. Mestres, et al. (2007). "In silico pharmacology for drug discovery: methods for virtual ligand screening and profiling," British JI of Pharmacology 152: 9-20.
Bantscheff, M, et al. (2007) "Quantitative mass spectrometry in proteomics: a critical review." Anal Bioanal Chem 389: 1017-1031.
Kristjansdottir et al. (Journal of Proteome Research (2008) vol. 7, pp. 2812-2824).
Sylvester et al. (Journal of Proteome Research (2012) vol. 11, pp. 1521-1536).
Rhodes et al. (Computational Biology (2005) vol. 24, No. 8:951-959).
Aebersold, R. and M. Mann (2003). "Mass spectrometry-based proteomics." Nature 422(6928): 198-207.
Craig, R. and R. C. Beavis (2003). "A method for reducing the time . . . with . . . mass spectra."Rapid Commun Mass Spectrom 17(20): 2310-6.
D'Agostino, R. B., A. Belanger, et al. (1990). "A Suggestion for Using . . . Test of Normality." The American Statistician 44(4): 316-321.
Eng, J.K., A.L. McCormack, et al. (1994). "An approach . . . mass spectral data . . . " J. of The Am. Soc. for Mass Spectrometry 5(11): 976-989.

(Continued)

*Primary Examiner* — Lori A. Clow
(74) *Attorney, Agent, or Firm* — Inventive Law Inc.; Jim H. Salter

(57) ABSTRACT

This invention is a novel method for analysis of data that is produced by test equipment. The preferred embodiment is data produced by liquid chromatography tandem mass spectrometry (LC-MS/MS) equipment, using industry standard methods to generate the initial data from the test equipment. The invention is a method for processing of the data to promptly produce accurate, reliable, and meaningful data that can be used for critical decisions. The unique benefit of the method is to correct the multiple measurement and calculation errors that are inherent in the operation of laboratory equipment. Prior methods result in errors based on circumstances that are difficult to control, accuracy-related errors in machine measurements, and fundamental mathematical errors in the data processing software that used with the laboratory equipment. As an added benefit, this novel method allows comprehensive simultaneous measurement and calculation of correlation of any and all peptide pairs in a single measurement, with the capability to support repeated measurements with changed conditions over time. This novel method allows robust, detailed, and comprehensive measurements of peptide activity and function, which results in substantial improvements over prior methods in accuracy, reliability, and efficiency.

6 Claims, 12 Drawing Sheets

(56) References Cited

OTHER PUBLICATIONS

Gavin, A. C., M. Bosche, et al. (2002). "Functional organization of the yeast proteome by systematic analysis . . . ." nature 415(6868): 141-7.

Gygi, S. P. and R. H. Aebersold (1999). "Absolute quantitation of 2-D protein spots." Methods in molecular biology 112: 417-421.

Han, M. H., D. K Han, et al. (2001). "Effects of protein kinase CK2 . . . on . . . acid-preferring phospholipase: A1." J Biol Chem 276(29): 27698-708.

Hanash, S. (2003). "Disease proteomics." Nature 422(6928): 226-32.

Huang D., B. Sherman, et al. (2007). "The DAVID Gene Functional Classification Tool . . . " Genome Biotogy 8, pp. R183-R183.16.

Keller, A., A. I. Nesvizhskii, et al. (2002). "Empirical statistical model to estimate the accuracy . . . by MS/MS . . . " Anal Chem 74(20): 5383-92.

Kitano, H. (2002). "Systems biology: a brief overview." Science 295(560): 1662-1664.

Kristhansdottir, K., D. Wolfgeher, et al. (2008), "Phosphoprotein profiling by PA-GeLC-MS/MS." J Proteome Res 7(7): pp. 2812-2824.

Kuster B., M. Schirle, et al. (2005). "Innovation: Scoring proteomes with . . . peptide probes." Nature Reviews Molecular Cell Biology 6: 577-583.

Li X. J., Zhang. et al. (2003). "Automated statistical analysis of . . . data generated by . . . mass spectrometry." Anal Chem 75(23): 6648-57.

Ma, B., K. Zhang, et al. (2003), "PEAKS: Powerful software for . . . mass spectrometry" Rapid Comm. in Mass Spectrometry 17(20): 2337-2342.

Maccoss, M. J., C. C. Wu, et al. (2002). "Probability-Based . . . Idenitifications Using . . . SEQUEST . . . "Anal Chem 74(21): 5593-5599.

Mason, C. J., T. M. Therneau, et al. (2007), "A method for . . . interpreting mass spectra . . . " Mol Cell Proteomics 6(2): 305-18.

Mootha, V. K., J. BunkenBorg, et al. (2003). "Integrated analysis of . . . mouse mitochondria." Cell 115(5): 629-640.

Pedrioli, P. G. A., J. K. Eng, et al. (2004). "A . . . representaion of mass spectrometry data . . . " Nature Biotecnnology 22(11): 1459-1466.

Perkins, D. N., D. J. C. Pappin, et al. (1999), "Probability-based protein identification . . . " Electrophoresis 20(18): 3551-3567.

Rauch, A., M. Bellew, et al. (2006). "Computational Proteomics Analysis Systems (CPAS) . . . " J Proteome Res 5(1): 112-21.

Reineke, D. M., J. Baggett, et al. (2003). ". . . the Effect of Skewness, Kurtosis, and Shifting . . . " Journal of Statistics Education 11(3):1-3.

Searle B. C. (2010). "Scaffold: A . . . tool for validating MS/MS-based proteomic studies." Proteomics 10(6): 1265-1269.

Shannon, P., A. Markiel, et al. (2003). "Cytoscape: A Software . . . for . . . Models of Biomolecular Interaction . . . " Genome Research 13: 2498-2504.

Volchenboum, S. L., K. Kristjansdottir, et al. (2009). "Rapid validation of Mascot search results . . . " Mol Cell Proteomics 8(8): 2011-22.

Yang, C., C. Yang, et al. (2010). "A regularized regression method for peptide quantification." Journal of Proteome Research 9(5):2705-2712.

Yates III, J. R., J. K. Eng, et al. (1995). "Method to Correlate . . . Mass Spectra . . . to . . . Database . . . " Analytical chemistry 67(8): 1426-1436.

Zeeberg, B. R., W. Feng. et al. (2003). "GoMiner: . . . interpretation of genomic and proteomic data." Genome Biol 4(4): R28.

| Scan Cutoff | | Delta Mass | | Ratio | | Mol. Weight | | PS Count | | # Pass | |
|---|---|---|---|---|---|---|---|---|---|---|---|
| Filter | Fail | Filter | Fail | Filter | Fail | Filter | Fail | Filter | Fail | PS | Gene |
| 0 | 0 | None | 0 | 0 | 0 | Infinity | 0 | 0 | 0 | 6570 | 1234 |
| 5 | 59 | 2 | 6570 | 0.01 | 58 | 1.5 | 362 | 1 | 0 | 0 | 0 |
| 5 | 59 | 4 | 619 | 0.01 | 58 | 1.5 | 362 | 1 | 343 | 5483 | 806 |
| 10 | 59 | 4 | 619 | 0.05 | 349 | 1 | 695 | 1 | 336 | 5354 | 795 |
| 25 | 299 | 4 | 619 | 0.1 | 586 | 0.5 | 1578 | 1 | 302 | 4950 | 742 |
| 50 | 1769 | 4 | 619 | 0.2 | 1011 | 0.2 | 2892 | 2 | 607 | 3246 | 378 |
| 100 | 5882 | 4 | 619 | 0.5 | 3125 | 0 | 5004 | 4 | 214 | 174 | 17 |

Fig 5

|  | Experiment 1 | Experiment 2 |
|---|---|---|
| Total Peptides Used | 4976 | 5046 |
| Total Genes | 720 | 749 |
| Fail Skewness | 444 | 476 |
| Fail Kurtosis | 150 | 179 |
| Fail D'Agostino's p-value | 37 | 31 |
| Fail p-value | 59 | 38 |
| Statistically significant Genes | 29 | 25 |
| Heuristically significant Genes | 114 | 130 |
| Total Keywords | 340 | 349 |
| Fail Skewness | 104 | 108 |
| Fail Kurtosis | 84 | 82 |
| Fail D'Agostino's p-value | 49 | 33 |
| Fail p-value | 21 | 73 |
| Statistically significant Keywords | 83 | 54 |
| Heuristically significant Keywords | 72 | 26 |

Fig 7

|  | Cardiomyopathy | Cell Adhesion | Chaperone | Dynein | Epidermolysis bullosa | Glycogen metabolism | Integrin | Kinase | Neurodegeneration | Prenylation | Protease | S/T Kinase | Transferase |
|---|---|---|---|---|---|---|---|---|---|---|---|---|---|
|  | 1 | 2 | 3 | 4 | 5 | 6 | 7 | 8 | 9 | 10 | 11 | 12 | 13 |
| 1 Cardiomyopathy |  | 0.091 |  |  |  |  |  |  |  | 0.063 |  |  |  |
| 2 Cell Adhesion | 0.091 |  |  |  | 0.100 |  | 0.300 |  |  | 0.042 |  |  |  |
| 3 Chaperone |  |  |  |  |  |  |  |  | 0.031 | 0.049 |  |  |  |
| 4 Dynein |  |  |  |  |  |  |  |  | 0.167 |  |  |  |  |
| 5 Epidermolysis bullosa |  | 0.100 |  |  |  |  | 0.333 |  |  |  |  |  |  |
| 6 Glycogen metabolism |  |  |  |  |  |  |  |  |  |  |  |  | 0.069 |
| 7 Integrin |  | 0.300 |  |  | 0.333 |  |  |  |  |  |  |  |  |
| 8 Kinase |  |  |  |  |  |  |  |  |  |  |  | 0.733 | 0.056 |
| 9 Neurodegeneration |  |  | 0.031 | 0.017 |  |  |  |  |  |  | 0.063 |  |  |
| 10 Prenylation | 0.060 | 0.042 | 0.049 |  |  |  |  |  |  |  |  |  |  |
| 11 Protease |  |  |  |  |  |  |  |  | 0.063 |  |  |  |  |
| 12 S/T Kinase |  |  |  |  |  |  |  | 0.733 |  |  |  |  | 0.393 |
| 13 Transferase |  |  |  |  |  | 0.069 |  | 0.056 |  |  |  | 0.393 |  |

Fig 10

METHOD FOR QUANTITATIVE ANALYSIS OF COMPLEX PROTEOMIC DATA

PRIORITY PATENT APPLICATION

This patent application is a continuation patent application drawing priority from U.S. patent application Ser. No. 13/068,026; filed May 2, 2011. The entire disclosure of the referenced patent application is considered part of the disclosure of the present application and is hereby incorporated by reference herein in its entirety.

STATEMENT REGARDING FEDERALLY SPONSORED RESEARCH OR DEVELOPMENT

A portion of the research activities involved in the refinement of the methods described herein was supported by U.S. government funding from the National Institutes of Health, listed under NIH Funding Agreement Numbers HG003864 and CA 126764.

COMPUTER PROGRAM LISTING APPENDIX

Computer software is attached in four compact discs, which are two identical sets of Disc One and Disc Two. The contents of the compact Disc One and Disc Two are incorporated by reference as part of this application. Disc One contains one ASCII file which is the instructions, written in Java computer programming language, of the sequence of calculation procedures that are the preferred embodiment for processing of complex data produced by laboratory equipment. Disc Two contains one ASCII file which represents the screened and processed data from typical test results in a useful output format. The source code and data output formats perform under either Windows or Macintosh operating systems. The data shown on Disc Two is an exhibition of results from typical mass spectrometry measurements. This computer software processes ambiguous test results into statistically significant data that is useful for showing the relationships between active elements within a complex system, such as the immune response communications network within an organism. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field of the Invention

The present invention relates to data processing methods that store, search retrieve and process cellular and biochemical information efficiently. The invention is a method that offers substantial benefits as contrasted with prior methods, to allow extremely accurate analysis of complex proteomic data produced by test equipment. More specifically, the method uses the data output of mass spectrometry equipment to produce refined measurements of protein functions and to infer protein interactions, including functions over a complex network of protein interactions within and between biological cells. The resulting information identifies and describes the significant functional relationships for each protein within a group of proteins that are components of a larger biological system. The biological system may be a single cell, a group of cells, or an entire organism. This unique method includes the following functions:

(a) accurate calculation of the relative abundance and activity of each protein for each functionally relevant categorical grouping, based on the measurements from laboratory test equipment, gene and protein sequence data from an external database, and the standard software that is used with the mass spectrometry equipment.

(b) multiple screening to reject errors, sorting by specified criteria, and specification of the functional relevance of proteins within a biological system. Based on sequential measurements over time or following a controlled change in conditions, the calculations include the amount of incremental change in the activity of proteins, and the correlation of activity and patterns of activity to identify and measure the functionally relevant classifications, for all possible combinations and permutations between all observed peptides, proteins, and functional categories.

(c) detailed description of the calculated results in a manner that shows the structure of the complex relationships, as a graphic pattern than can be readily understood by the equipment operator.

Description of the Related Art

As a result of the advances in genomic sequencing technologies, complete genomic sequences have been derived for several species. Before these technological advances, it was not possible to determine the complete sequence of deoxyribonucleic acids (DNA) in an organism and organize the sequence into functional genes. However, in recent years the technology for sequencing genes has advanced so that it is not only feasible to determine complete genomic sequences but also to quantitatively measure the abundance of every expressed gene, based on mRNA levels for every gene found in a cell.

Nevertheless, analyses of gene sequence and abundance do not provide sufficient information to explain the mechanism, functions, and activity of biological processes. Proteins are essential for the control and execution of virtually every biological process. Accurate correlations between gene sequences and protein functions are limited by the degree of similarity between sequences and the availability of prior experimental results that demonstrate correlation or causation for protein function under specified conditions. Genomic data fails to provide correlations between biological processes and protein activities. The state of protein activity in a cell cannot be determined by gene sequence or the expression level of the corresponding mRNA transcript. Therefore, novel methods are required to monitor biological processes in terms of protein function.

Determining the complete sequence of DNA and mRNA for an organism is only a partial solution to the larger issues of how to understand basic biological functions. Advances in genomic research were based in large part on developments in computer technology and insightful software design. Using new computational approaches researchers were able to generate, store, organize and analyze large amounts of sequencing data. The investigation of protein function at a similar scale also requires advances in computation and software design so that large amounts of complex data can be accurately analyzed. Software designed for the analysis of protein function at a cellular and organismal scale faces separate challenges than those considered in genomic research.

The critical unsolved issue is to accurately describe the functions of all proteins that are derived from the genome, in terms of protein activity and functions over time or following controlled changes in conditions. This protein activity must also be understood with regard to the interactions of multiple proteins within a total system. The identity of each protein is based on messenger RNA transcribed from the DNA sequence of a gene. The function of each protein is determined by changing conditions within and around each cell. Accordingly, measurement of protein functions, and description of protein interactions and complex interrelationships, is separate from sequence identity.

Proteomics is the study of protein activity, functions and interactions. The scope of protein interactions depends on the extent of the cellular signaling network. Accordingly, the effects of protein activity may include interactions within a cell, interrelated interactions among an integrated group of cells, or complex interactions within an entire biological entity. With current technology, the critical unsolved issues include accurate measurement of protein function and activity, description of the protein-to-protein interactions, and the effects of selected compounds for modulation of protein activity. Specialized equipment and methods are a practical necessity to approach new challenges in the field of proteomics.

The process of inter- and intracellular signaling involves a complex network of protein interactions that change rapidly in response to different stimuli. Despite the critical importance of protein activity and protein interactions, the accurate measurement of incremental changes in function over time has remained an unresolved issue. The accurate measurement of protein function is made particularly difficult by the frequent modulation of post-translational modifications that significantly alter protein function. Changes to protein function are associated with critical human diseases, such as sepsis, emphysema, and various forms of cancer. To address the mechanistic cause and progression of these diseases, it is essential to measure biological activity in terms of quantitative changes in protein function.

Overview of Proteomics Technology

Proteome analysis is typically based on the separation of complex protein samples by one-dimensional or two-dimensional gel electrophoresis (2DE) and liquid chromatography, followed by identification of the individual protein species (Gygi and Aebersold 1999). Spectrometric techniques and basic computer algorithms have been designed to rapidly identify proteins by matching peptide mass spectra data to protein and translated nucleic acid sequence databases (Eng, McCormack et al. 1994; Yates III, Eng et al. 1995).

The prior art is shown in the listing of patents and relevant technical publications. The failures of prior art are demonstrated by the omissions in prior patents. The methods proposed by prior patents focus on the accurate identification of proteins by amino acid sequence and modifications. For example, prior art recognizes the need to consider the statistical significance of possibly erroneous matches (Sachs, 2005, page 18, lines 49-51) and potential errors caused by incomplete sequence databases, incomplete splicing, protein modifications, or protein polymorphism (Emili, 2005, paragraph 0199). It is recognized that reliance on the standard software contained in an automatic search engine (e.g., Mascot) and a protein database results in a great number of errors, termed pseudo-positive results, but the proposed solutions do not provide a standard method to prevent or correct the identified errors (Oda, 2008, paragraph 2065). The establishment of a custom database to correct errors in a single run (Oda, 2008, paragraphs 2065-2068) merely confounds the problem because the custom database is not shared or verified by other unbiased independent investigators.

Quantitative methods for proteomic research assign measures of abundance to identified proteins. To date, quantitative proteomic methods lag behind methods for the identification of proteins from complex samples. Currently applied quantitative methods fail to provide statistical confidence intervals and correct for sources of measurement error. For example, exclusion of measured data through the subjective exclusion of outliers (Sachs, 2005, page 18, lines 54-60) results in data that is the result of investigator selection of preferred data, as contrasted to empirical and unbiased measurement. A recent patent describes a method for measurement of protein phosphorylation with mass spectrometry, but no method to correct the underlying software efforts (Hunt, 2006, page 6, lines 5-15). Similarly, a recent patent describes methods to provide a baseline for quantitative comparison through internal controls, but no method to screen out erroneous equipment measurements or incorrect software calculations (Aebersold, 2009, page 7, lines 12-22).

Prior methods note that keyword categories are useful to selectively focus on biological functions of interest within a database (Yamashita, 2010, page 8, lines 10-15), (James 2007, paragraph 0013). However, the prior methods do not include quantitative measures of abundance for keyword categories nor do they calculate statistical correlations between all observed categories. Protein sequence similarity alone has also been used to infer functional similarity and molecular interactions (Mallal, 2006, paragraphs 0007-0012). However, this method merely compares selected sequences and does not provide for a quantitative measure of the degree of shared functionality between all possible proteins within and between samples.

Significantly, the widely used standard methods and software for mass spectrometry analyses are based on the original formats and codes designed over a decade ago. These early developments contained fundamental errors. Accordingly, it is not surprising that the current software and associated methods fail to correct critical calculation and measurement errors. Recent studies by several investigators demonstrate that current methods exhibit significant errors in repeatability and reproducibility, so that typical results cannot be reliably reproduced even with the same machine, same sample, and same operator (Tabb, Vega-Montoto et al. 2010). The existing computer software, test protocol, and screening processes have not kept pace with the current need for analytical details that precisely describe protein function within an interaction network.

Accurate analysis of protein functions present difficult technical obstacles. Protein functions are interrelated as shown by the complex signaling within and among cells. Accordingly, measurement of protein functions over time is a continuing challenge. The required measurements include accurate identification, physical count of abundance, extent of activity, and the extent of interaction between any two proteins. The widely accepted equipment, consisting of liquid chromatography combined with tandem mass spectrometry (LC-MS/MS), is adequate to provide the essential input data. However, substantial improvements in software and computational methods are necessary to correct errors that result from the use of standard but outdated software to analyze data obtained by mass spectrometry.

Current Test Procedures For Mass Spectrometry Equipment

Continuing technical developments have allowed improvements in mass spectrometry equipment and procedures. The following is a typical procedure for the identification of proteins using mass spectrometry. Samples are prepared from cell lysates that contain tens of thousands of distinct protein species. The sample can be simplified by separating proteins based on size using gel electrophoresis and isolating slices of the gel that contain only several hundred proteins per slice. Handling each slice separately allows the identification of a more complete portion of the original sample. Sample proteins are broken up into short segments termed peptides using a proteolytic enzyme. This resulting mixture of peptides is then separated by liquid chromatography (LC).

This separated mixture is injected into the mass spectrometer, which measures the mass/charge ratio (m/z) for ionized peptides. Then, the MS equipment selects individual peptide ions, fragments them using low-energy collisions, and measures the mass of the ion fragments to obtain amino acid sequence information. The observed m/z ratio of the intact and fragmented peptide ions allows inference of the amino acid sequence. External software accomplishes this by matching fragmentation data to sequence databases. Meanwhile, the intensity of the intact peptide ions allows measurement of relative abundance for species that share the same ionization potential. Internal standards have been developed for the purpose of providing a means for accurate quantitation. A typical MS/MS test procedure takes several hours and may produce hundreds of thousands of line items.

Specialized software is required to interpret the data produced by mass spectrometry equipment, with emphasis on matching the measured sequence to a database that allows accurate identification of each protein. Over the past 16 years, several data analysis programs have been developed for protein identification (Xu and Ma 2006). Typical commercially available software includes: Sequest (Eng, McCormack et al. 1994; MacCoss, Wu et al. 2002; Sachs, Wiener et al. 2005), Mascot (Matrix Science) (Perkins, Pappin et al. 1999), and Peaks (Ma, Zhang et al. 2003). Many additional programs have been developed, typically using different scoring functions, and different methods for error correction and interpretation of the MS/MS results.

However, despite the many alternative mass spectrometry software programs that are available, these programs exhibit serious deficiencies that prevent accurate measurement and detailed analyses. Based on the identified deficiencies in the prior methods, there is basic need for a novel method to meet the requirements. The novel method must correct errors in the mass spectrometry measurements, correct errors in the software used by the MS/MS equipment, and screen out results that fail to meet accuracy criteria. The novel software must allow accurate measurement of protein functions and the full range of multiple protein-protein interactions.

With prior methods, test results were typically inconclusive, due to the inherent complexity in the identification of major biological trends and errors in the measurement of relative protein abundance.

The Need For New Mass Spectrometry Data Analysis Methods

Significantly, the prior methods and software exhibit serious unresolved issues, such as multiple identification errors, counting errors, and even basic mathematical errors in the original software code. Importantly, the existing methods do not produce the details necessary to derive protein function, or to measure statistical correlations that allow inference of protein-protein interaction for each protein pair in the sample. Accordingly, the existing methods fail to provide the information required for important protein analysis decisions, such as the formulation and design of new compounds for diagnosis or treatment of disease.

Thorough use of mass spectrometry equipment and related methods have resulted in clear identification of the requirements for new methods. Accurate measurement and complete disclosure of all measured data is necessary. The measurements must allow precise and unambiguous identification of each protein from the peptide samples. As a practical necessity, the new methods must be able to use the data output of existing software and testing methods, so that each existing laboratory is not required to purchase new equipment or to learn to use entirely different methods. The transition from the old methods to the new method should be without severe obstacles.

There is a need for an enhanced spectrum of information. Mere identification and classification is not sufficient. The data must support calculation of protein functions and protein interactions over time or following controlled changes in conditions. Detailed measurements of protein activity are necessary to describe and understand cellular signaling, deficiencies in the immune system, and the effects of modulation of signaling through inhibitors. This detailed information as to protein function is necessary to design effective treatments of critical diseases, such as cancer or sepsis.

SUMMARY OF THE INVENTION

Embodiments of the invention described herein provide a method of analysis and translation of data that represents chemical structures such as proteins, and fragments thereof such as peptides, into information that can be used for critical decisions, based on the measured activity and function of specific proteins and the complex interaction of an entire group of proteins. In the preferred embodiment, the method would provide a firm foundation for decisions regarding the effects of attempted modulation of protein activity, such as the functional effects of an inhibitor on kinase activity.

The invention is a novel calculation method that allows the existing data output of the mass spectrometry equipment to be processed in a unique manner so that the resulting information output is accurate and reliable. The invention provides accurate identification of each protein from the peptide segment, based on a detailed review of specific criteria to assure that errors from the mass spectrometry equipment and associated software are rejected. Also, the invention calculates and displays the amount of interaction between all pairs of genes and keyword categories in the sample. Based on this invention, accurate information is provided for critical issues, such as accurate measurement of protein functions and protein network signaling.

Benefits and Advantages of the New Method

Significantly, the new method provides a practical, feasible solution to unsolved critical issues. The new method provides multiple screening of errors, to provide refined data that allows accurate identification of each and every protein. The new method allows identification of the measured intensity of the protein-protein interaction for each and every pair of proteins. In addition, the novel method displays the results in a manner that converts the complexity into a meaningful pattern, so that the investigator can understand the results.

The new methods allow analyses that clearly show the extent of protein activity within a sample, and to clearly detect and describe the correlation of activity for each pair of proteins. The novel methods correct the various measurement and counting errors that are now included in the data output from current mass spectrometry equipment, due to the outdated software. The new methods solve the critical problems of verification of protein identity, measurement of abundance and activity for each identified protein, and the measured amount of interaction between all possible combinations of any two proteins. The novel methods provide a valuable solution to these previously unresolved issues.

The invention includes multiple screening and correction of calculation errors inherent in the data output from the mass spectrometry equipment. As a unique benefit, the new method provides the data in a format that allows pattern recognition to support understanding of the test results. The complexity is distilled into a structured format that allows reasoned conclusions, supported by statistical tests of confidence in the data presented.

The invention provides a method for to measure the correlation and co-activity or all combinations and permutations for any two proteins within the sample. Accordingly, the method allows accurate measurement and comprehensive description of effects of inhibitors on protein activity. Significantly, based on separate measurements over time, the functional effect of an inhibitor on protein activity can be derived, based on plots of data that describe incremental changes over time, and the resulting mathematical formulas the show the underlying relationships. Based on accurate measurements, the invention supports meaningful tests of the effects over time of compounds that modulate protein activity, protein response to changes to communication network signaling, and the selection of chemical probes, candidate compounds, or molecular targets.

Pattern recognition is a practical requirement for complex data sets, which may have inconsistent details, or conflicting criteria, or subtle relationships. This pattern recognition is a practical necessity because of the amount of data that is involved with proteomics is so voluminous that the relevant data cannot be reasonably viewed and understood by a human within the time required for decisions and actions.

Specialized software is a practical necessity to sort data, compare measurements with known information, derive relationships, and display the data results in a manner that allows recognition of the fundamental patterns by a human observer. Based on this pattern recognition, the human can make decisions and take actions based on facts, as contrasted to conflicting opinions or a welter of disorganized information. Proteomics involves such a vast volume of data, relationships, and contingent effects that a human expert cannot easily understand the underlying patterns without a clear display of the complex data. Significantly, this invention displays the underlying pattern from a large database with complex test data in a manner than allows prompt understanding and decision. This invention produces outputs in the form of a tabular listing and graphical displays which can be ready and quickly understood by a human.

The data results describe protein activity, and protein-protein interaction for each possible pair of proteins. Based on iterative runs, the method allows description of network configurations, and the functional relationships of protein function over time.

Figure 2:
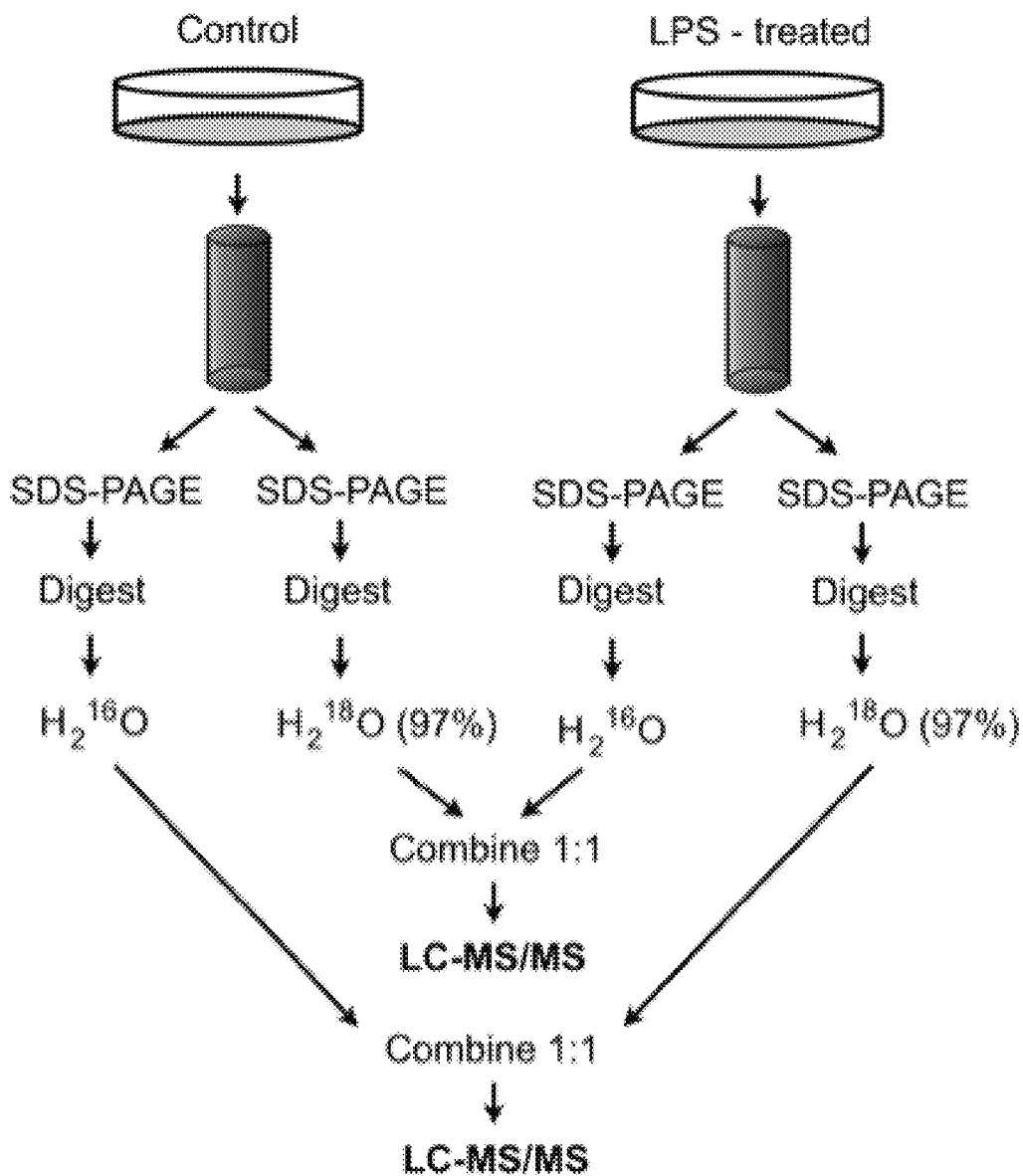

FIG. 2 is a flow diagram that depicts the establishment of a control, as technical replicates with reverse isotopic labeling, by tagging with light and heavy molecular characteristics, and with separate calculation of the results for the two conditions, to establish a foundation for comparison of the control versus the LPS treated samples.

Figure 3:
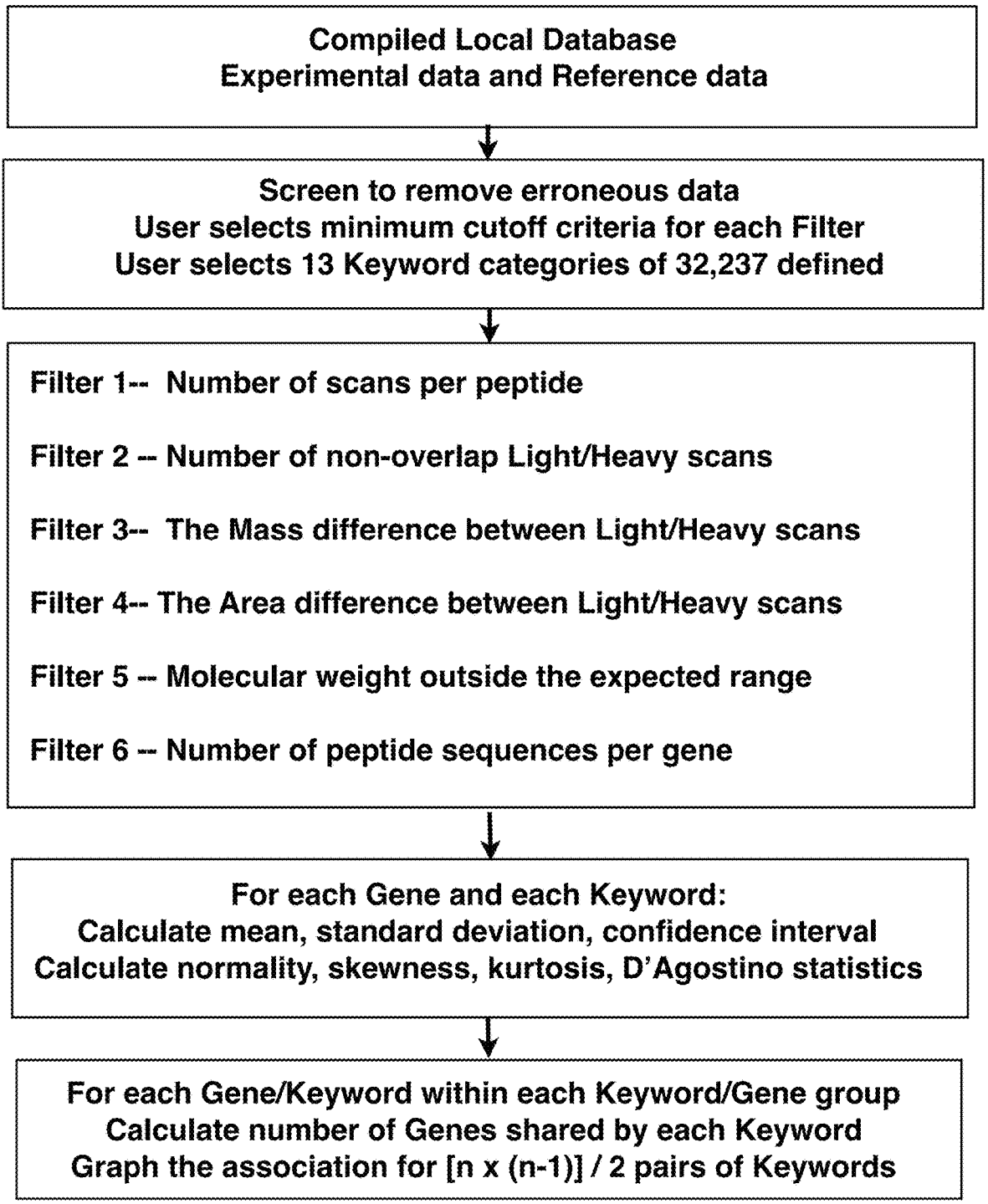

FIG. 3 is a flow diagram that depicts the major steps for the inventive method, including screening with 6 separate user-defined filters, screening for statistical significance, and grouping of results by gene and keyword category. The results include detailed reports of passed versus rejected data, and the amount of protein-protein interaction for each possible combination and permutation of protein pairs.

Figure 4:
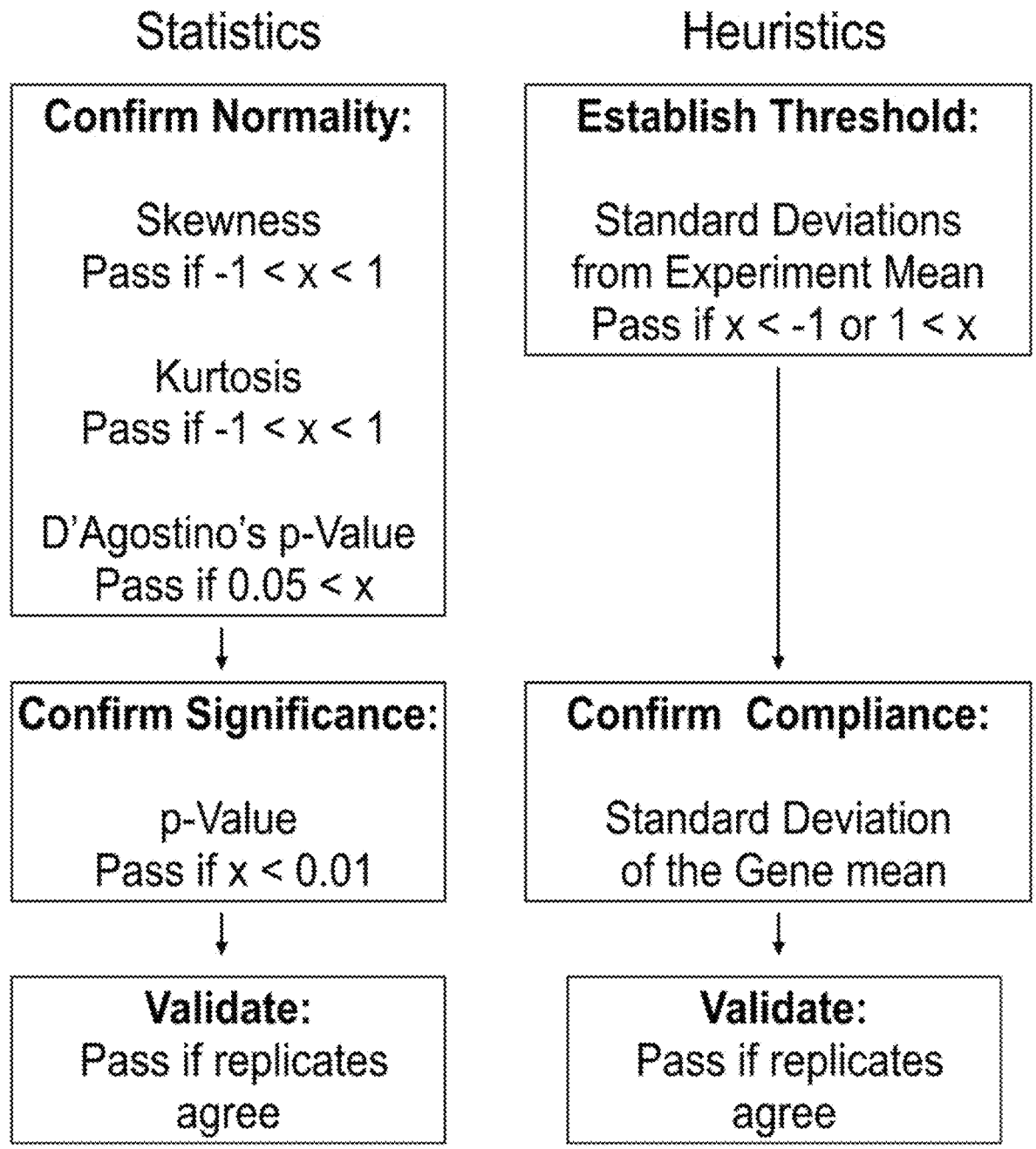

FIG. 4 is a flow diagram that depicts the threshold values for statistics and heuristics. Statistical inference tests whether the results occurred due to random events. Heuristics tests whether the results are close to an approximate solution by an alternative method. For either approach, the results are verified by comparison to replicates.

FIG. 5 is a table that depicts specific rejection criteria for four of the six independent screens which act to accept valid data and to reject erroneous data, based on criteria established by the investigator with regard to basic biochemical relationships. The post-processing filters control the quality of data that is used to derive the calculated results. For this test, over half of the 15,925 peptide sequences (PS) that were accepted by standard methods were rejected due to the measurement and data processing errors identified by the inventive methods.

Figure 6:
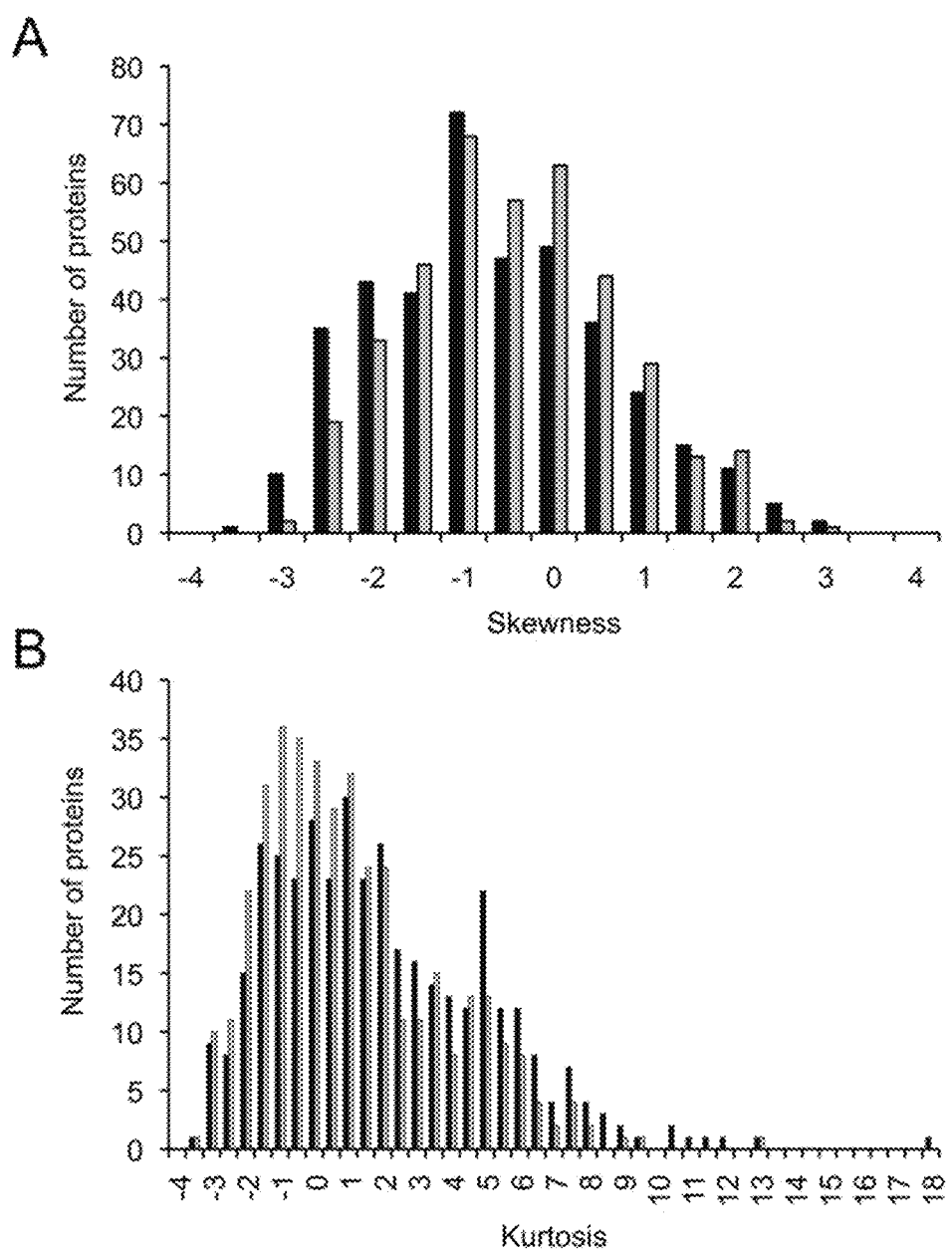

FIG. 6A is a chart that depicts the variation from a normal distribution due to skewness. FIG. 6B shows the variation from a normal distribution due to kurtosis. In black, the frequency distribution is shown for heavy-labeled vs. light-labeled peptide ion areas. In grey, the frequency distribution is shown for heavy-labeled vs. total paired peptide ion areas. The frequency distribution is calculated from log 2-transformed fold change ratios.

FIG. 7 is a table that depicts the large proportion of erroneous results based on standard methods, and the effect of the statistical significance filters provided by the invention. For Experiment 1, from 4,796 peptides, although 720 genes were recognized by the standard methods, after rejecting insignificant data only 29 genes remained. Similarly, for Experiment 2, analysis using standard methods for 5,046 peptides resulted in 749 genes recognized, but only 25 genes passed the statistical filters. A similar proportion of errors are recognized when screened by keyword categories.

Figure 8:
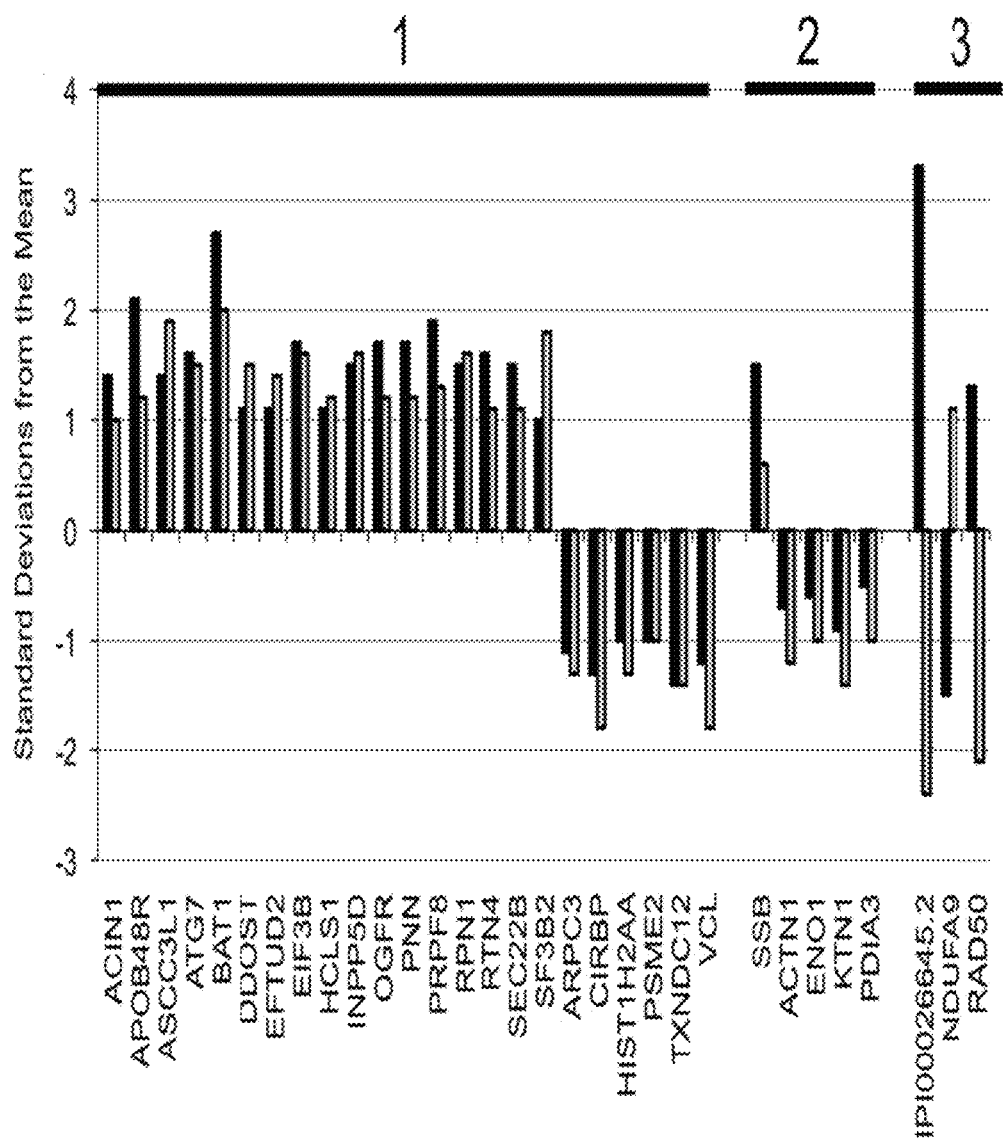

FIG. 8 is a chart that depicts a significant change in abundance in response to lipopolysaccharide (LPS), as compared to the control group, showing protein signaling response to gram negative bacteria. Experiment 1 is shown in black and Experiment 2 is shown in grey. Within Category 1 are the genes that changed more than one standard deviation from the total peptide population mean. Within Category 2 are the few genes with statistically significant means from the peptide population which passed normality constraints. Within Category 3 are results that are rejected because calculated results did not agree with experimental replicates.

Figure 9:
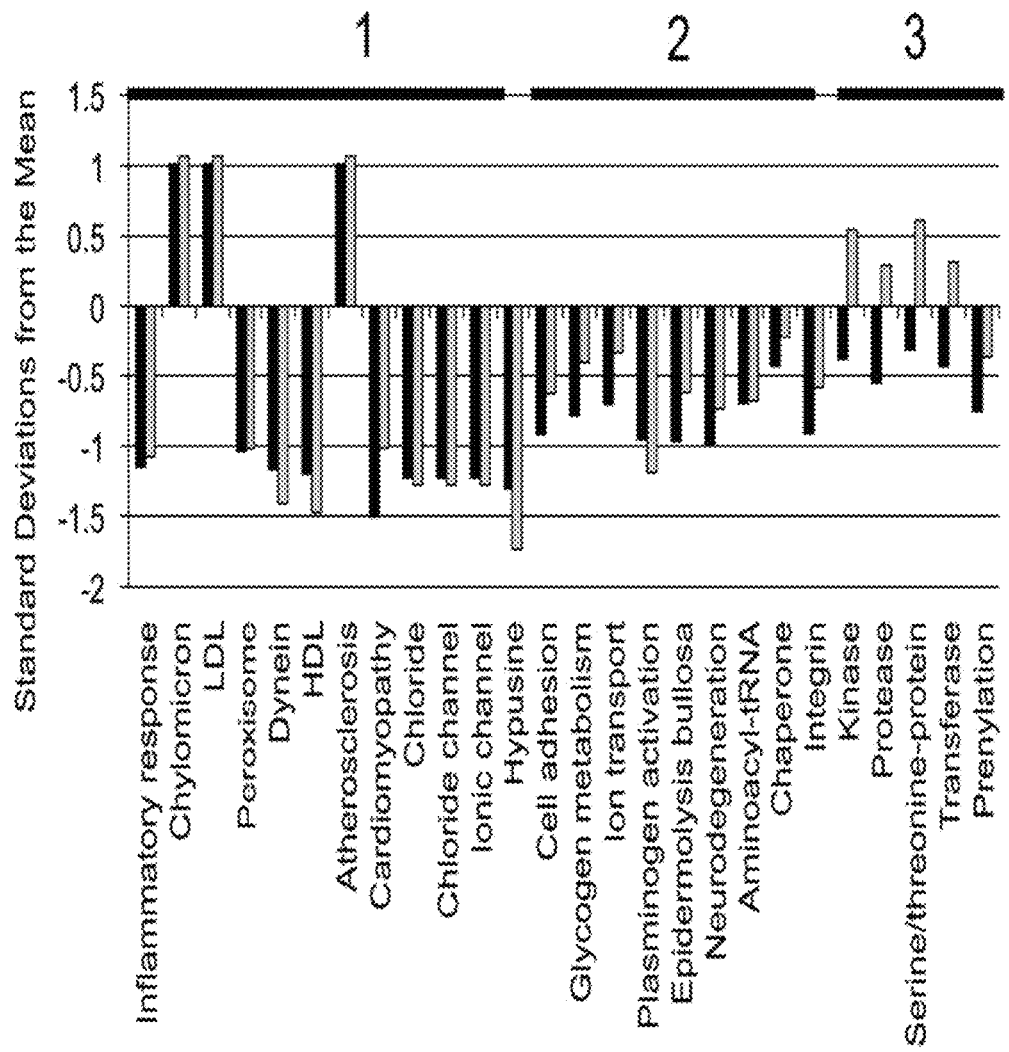

FIG. 9 is a chart that depicts results similar to FIG. 8, but with measurements grouped by keyword category instead of by gene. Within Category 1 are the keywords that changed more than one standard deviation from the total peptide population mean. Within Category 2 are the keywords with statistically significant means from the peptide population which passed normality constraints. Within Category 3 are results that are rejected because calculated results did not agree with experimental replicates.

FIG. 10 is a chart that depicts protein-protein interaction as shown by keyword categories for protein function. The number score for each pair depicts the amount of interaction, from 0 to 1.0.

Figure 11:
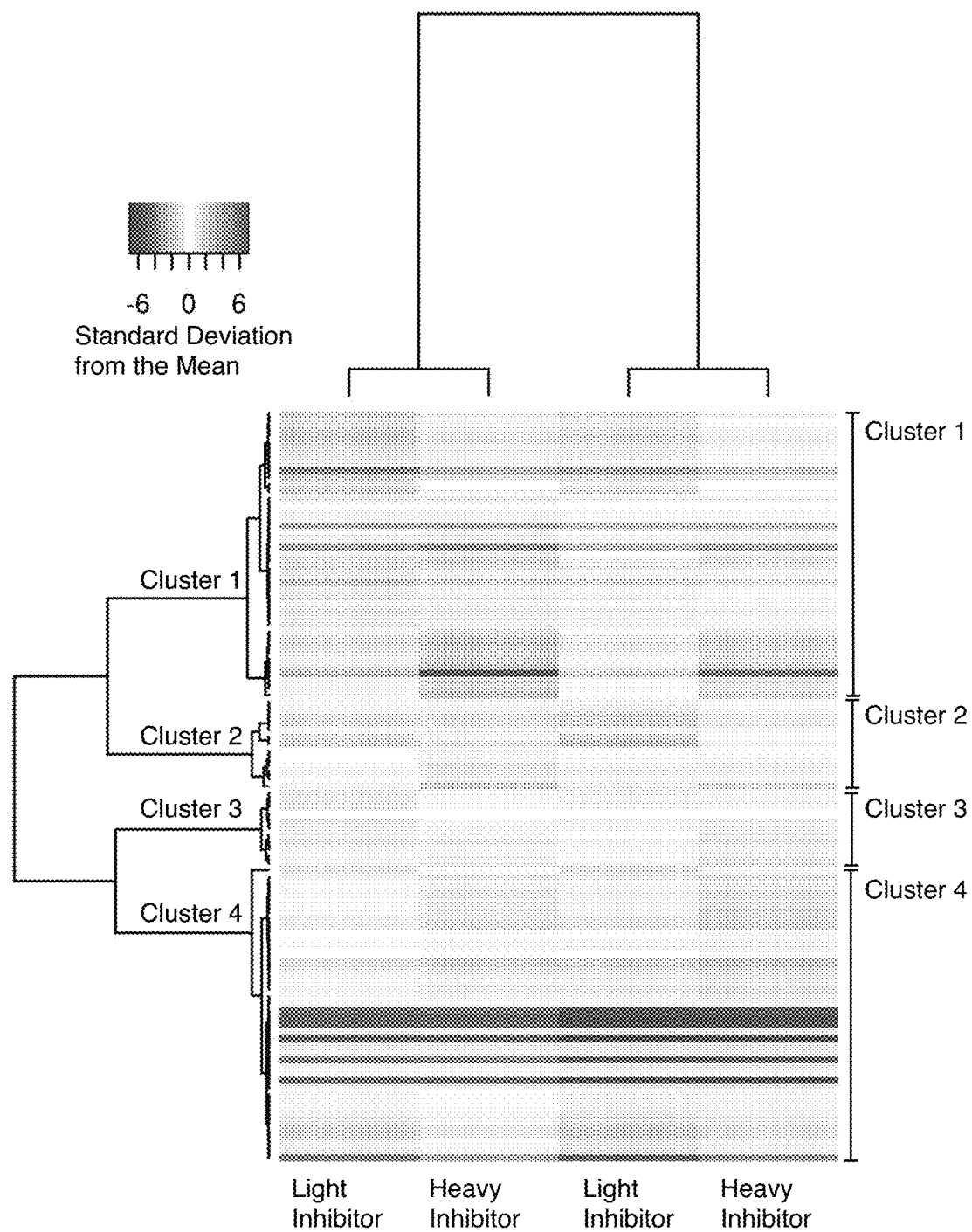

FIG. 11 is a chart that depicts the protein-protein interaction for specific genes with Akt inhibition of lipopolysaccharide (LPS), for both light and heavy isotope-labeled peptides.

Figure 12:
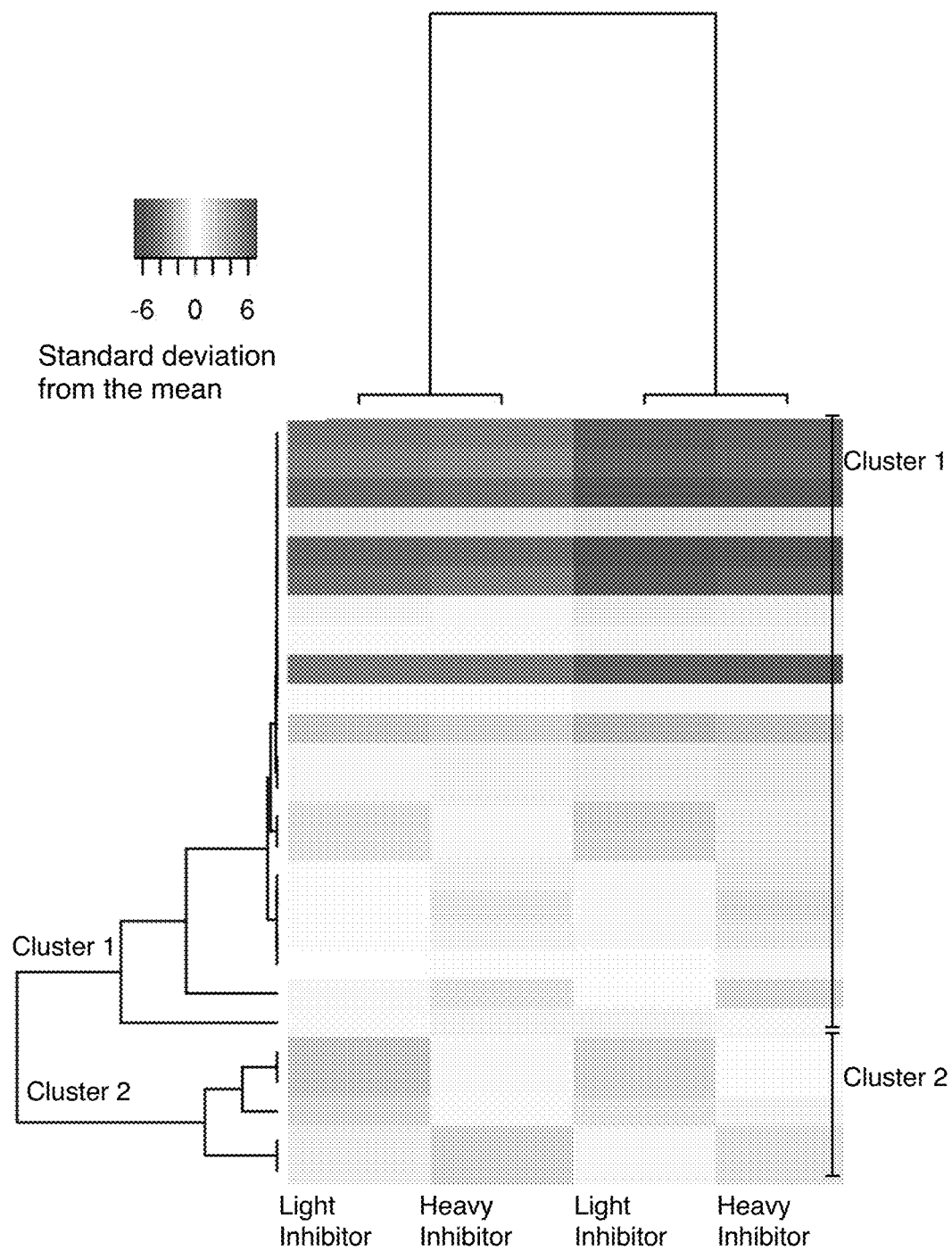

FIG. 12 is a chart that depicts the protein-protein interaction for specific keyword categories with Akt inhibition of lipopolysaccharide (LPS), for both light and heavy isotope-labeled peptides. The keyword grouping allows improved insight into the protein functions, as compared to grouping by genes.

DETAILED DESCRIPTION OF THE INVENTION

Discussion of Proteomics

Proteomics is the study of protein functions. By contrast, genomics is the study of gene functions. The complete set of proteins expressed by a cellular genome under specified conditions is popularly referred to as the proteome. Over the past decade, there has been a significant effort to comprehensively describe differences between cellular states by changes in the proteome. Differences in protein expression and modification have been used to investigate the pathology of disease processes (Hanash 2003) and highlight differences in gene regulation (Mootha, Bunkenborg et al. 2003). Technological advances allow increasingly efficient parallel quantitative analyses of protein abundance and modifications (Aebersold and Mann 2003).

The proteome is a more dynamic counterpart to the genome and proteomic experiments can generate a staggering amount of data despite incomplete sampling of all cellular proteins (Cox and Mann 2007). Nevertheless, the promise of proteome research as a tool for the identification of characteristic patterns of protein activity is critically hindered by the challenge to analyze and interpret proteomic data in a biological context. Computational approaches based on the compilation of observed molecular interactions have been developed to reference and build probable networks of protein activity (Kitano 2002; Joyce and Palsson 2006; Ekins, Mestres et al. 2007; Sharan, Ulitsky et al. 2007).

Despite the prior advances, the amount of time required to generate biologically reasonable hypotheses from proteomic data can be a significant challenge for data analysis. Techniques to systematically analyze protein networks will not be successful without a standardized method of data analysis that determines quantitative significance at a global scale and meaningfully organizes data using graphical aids for the visualization of patterns.

Mass spectrometry is one method of proteome investigation for which there are several mature software tools for the identification of peptide sequences, validation of these identifications and quantitation from raw spectral data. However, the unsolved issues include fundamental problems of interpreting and analyzing the resulting data (Aebersold and Mann 2003). The basic problems stem from outdated software and methods that did not keep pace with the challenges of proteomics.

As a fundamental requirement, the new method must accept the widely encountered formats of proteomic data and produce commonly accepted statistics to guide researchers to the genes of greatest interest. The application transparently incorporates heuristics that have been tested on extensive experimental research, so that the researcher has effective control over a large number of parameters. By contrast, existing mass spectrometry analytical software forces the user to accept hard coded parameters buried within the code.

As a unique advantage, this new approach provides the end user with a set of sieves for finding a range of interesting values instead of a drill for mining out a single value. One major part of this approach is the capacity for iterative analysis, to allow multiple analyses of the data using different criteria. With this new method, the researcher can efficiently analyze a batch of data to produce a specific set of results then modify the search parameters to generate another set of results.

This rapid iterative approach allows insight into the functional relationships, as contrasted to the slow process of detailed inspection of individual data points without getting any sense of the overall relationships. The novel methods allow the researcher to quickly discern the structure within the complexity. Ultimately the goal of many proteomic experiments is to provide a snapshot of groups of proteins involved in functional roles (Gavin, Bosche et al. 2002). This functional categorization of proteomic data is dependent on the availability of complete genome sequences and searchable databases with entry definitions.

While popular databases, such as Gene Ontology and UniProt, have defined sets of keywords for organizing genes, existing software will often use these solely for qualitative groupings and will not take full advantage of these features for quantitative analyses. Our application can use the keyword as a unit of statistical analysis, which provides larger sample sizes and a more global view of the data. The application can also explore relations between keywords, which has implications for network analysis. Moreover, this data may contain many false correlations.

As a basic requirement, the new method must use simple heuristics to filter and sort data, meaningfully organize the remaining data and apply intuitive statistical methods to highlight genes that showed significant changes. Several suites of software have been developed to work with raw data. This program does not deal with raw data. Instead, it organizes data and so that the user can interpret it. This requires filters to remove data of poor quality and sorting for easy comparisons at the level of peptides, genes, and experiments. It also requires statistics and heuristics so that decisions can be made according to a uniform application of values. The data are defined by a peptide, by a gene, or by a population of genes. Multiple variables are addressed systematically in a specified order.

A longstanding goal in biology has been to identify proteins that are indicative of inflammatory signaling events pertaining to the response of neutrophils to lipopolysaccharide. To accomplish this we needed a post-processing platform that was capable of calculating relative protein abundance and mapping identified proteins according to function. Several software suites are available to generate graphics from protein annotation notes derived from database searches. Existing software does not take into account functional overlap between categories. The software was designed for mass spectrometry but is applicable in theory to all proteomic analyses.

EXPERIMENTAL PROCEDURES

The following described procedures are the preferred embodiment for use of the invention. Improved procedures may be developed and the use of the improved procedures do not limit the scope or applications of the invention.

Sample Preparation

To provide a source of data that was rich in content for functional annotation and had been extensively analyzed through various methods in the past, we prepared a complex soluble protein sample from neutrophils activated by LPS. To normalize the conditions under which samples were prepared, the human promyelocytic HL-60 cell line (ATCC) was differentiated in culture using 1 µM ATRA, 6 pM 1α,25-Dihydroxyvitamin D3, and 30 ng/mL G-CSF in IMDM, supplemented with 20% FBS and 4 mM L-glutamine. Cells were activated via treatment with 100 ng/mL of lipopolysaccharide (LPS) from $E.$ $coli$ O111:B4 (List Biological Laboratories, Campbell, Calif.). The control sample was treated with an equal volume of double-distilled and autoclaved water. Cells were harvested, lysed, and enriched for phosphorylated proteins using the Pro-Q Diamond phospho-enrichment kit (Invitrogen, Carlsbad, Calif.), following kit instructions and as previously described (Kristjansdottir, Wolfgeher et al. 2008). Fractions were collected, concentrated, and washed with 0.25% CHAPS in 25 mM Tris, pH 7.5, by centrifugation at 4° C. using 10 kDa-cutoff concentrators (Millipore, Billerica, Mass.) for a final volume near 500 µL.

The total protein content of eluted fractions was determined by Bradford analysis (Pierce, Rockford, Ill.) using the average of triplicates. Total protein content was also qualitatively compared by the intensity of Coomassie staining (Thermo Scientific, Rockford, Ill.) following gel electrophoresis. LPS-treated and control samples were loaded at equal total protein content for separation on 4-12% NuPAGE gradient electrophoresis gels (Invitrogen) using MOPS SDS running buffer. Gels were cut into 11 vertical slices, combining 9 replicate lanes for each vertical slice to increase protein abundance per sample.

Gel slices were de-stained with 50% CH3CN in 100 mM NH4HCO3, pH 7.5, for 15 m, reduced with 20 mM TCEP in 50 mM NH4HCO3 for 30 m at 37° C., and acetylated with 50 mM iodoacetamide for 30 m in the dark. Gel slices were washed with ultrapure water and dehydrated in CH3CN for 5-10 m, which was removed by vacuum centrifugation. Proteins were digested in-gel by re-hydrating each gel slice with 2 µg of trypsin in 60 mM NH4HCO3 with 0.5 mM CaCl for 12 h at 37° C. Peptides were extracted from gel slices in two steps, starting with an aqueous extraction with 5% formic acid in water for 1 h and followed with an organic extraction with 5% formic acid in 50% CH3CN. Extractions from each step were centrifuged under vacuum separately, combined in water, and lyophilized.

Isotopic Labeling

Isotopic labeling by enzymatic incorporation of 16O and 18O was used for relative protein quantitation between LPS-treated and control samples. To label peptides at the carboxyl-terminus with 16O or 18O, samples were re-suspended in H216O or H218O and incubated with 30 µL of washed Mag-Trypsin beads (Clontech, Mountain view, Calif.) for 48 h at 37° C. The reaction was monitored by MALDI-TOF MS (4700 Voyager, Applied Biosystems, Foster City, Calif.). Beads were removed by magnetic separation, labeled samples were lyophilized and re-suspended in 2% CH3CN with 0.2% formic acid in water (mobile phase A) and mixed 1:1 (v/v).

Nanoscale LC-MS/MS

A total of 11 LC-MS/MS runs was performed per experiment, corresponding to the number of gel slices. Using an Eksigent AS1 autosampler and auxiliary isocratic pump (Eksigent Technologies, Livermore, Calif.), 10 µL injections were loaded at 10 µL/m onto a 2.5-µL Opti-Pak precolumn (Optimize Technologies, Oregon City, Oreg.) packed with 5 µm, 200 Å Michrom Magic C8 solid phase (Michrom BioResources, Inc., Auburn, Calif.) to remove contaminating salts. Peptides were separated at 350 nL/m on a 20-cm× 75-µm-inner diameter column packed with 5 µm, 200 Å Michrom Magic C18 solid phase (Michrom BioResources). A 90 m two-step chromatographic gradient was used that started with a slow separation from 5-50% B over 60 m followed by a rapid increase from 50-95% B over 10 m using 80% CH3CN, 10% n-propyl alcohol, and 0.2% formic acid in water as mobile phase B.

Samples were analyzed on an LTQ-Orbitrap Hybrid FT mass spectrometer (Thermo Scientific). Data were collected in full profile mode from m/z 375 to 1,950 at 60,000 resolving power with internal calibrant lock masses. The five most abundant double- and triple-charged precursors with a minimum signal of 8,000 between 375-1,600 m/z were subjected to collision-induced dissociation (CID) with 35% normalized collision energy, 30 ms activation time, and activation Q at 0.25. To reduce repeat analyses, dynamic exclusions were established for 60 s with an isolation width of 1.6 m/z units, for low and high mass exclusion of 0.8 m/z units each per precursor.

Database Searching

Thermo .raw files were converted to the mzXML format using ReAdW (from TPP version 4.1) and imported into the CPAS database organization and analysis application (version 9.10) (Rauch, Bellew et al. 2006). X!tandem (version 2.007.01.01.1) (Craig and Beavis 2003) identified peptides and proteins from fragment ion spectra of selected precursors using the non-redundant human international protein index (version 3.53) maintained at the European Bioinformatics Institute (EBI; Hinxton, United Kingdom). Parent ions required less than 20 ppm mass accuracy and greater than 90% matched molecular weight against expected values based on the PeptideProphet algorithm (Keller, Nesvizhskii et al. 2002).

Search parameters specified tryptic digestion and allowed only one missed cleavage per peptide. Cysteine acetylation from iodoacetamide treatment was set as a fixed modification. S-carbamoylmethylcysteine cyclization at the amino-terminus, pyroglutamic acid formation from glutamine and glutamate, oxidation of methionine, and single and double isotope label incorporation at lysine and arginine were considered variable modifications. Although distinct proteins within a family may share identical peptides, ambiguous assignments were grouped by a single protein identifier based on a representative group member following the law of parsimony.

Ion Current Integration

The XPRESS software (version 2.1, from TPP version 3.4) was used within CPAS to reconstruct peptide elution profiles (Han, Han et al. 2001). Peptide signal intensity was integrated over the number of MS scans in which a peptide was observed, thereby providing quantitative areas for 16O and 18O labeled peptides. XPRESS was not used to calculate protein abundance ratios from these areas.

Software Setup

The software described here interacted with a MySQL database that was populated with reference data used to filter and organize results. Keywords were defined by the total set of 32,378 terms in 13 categories from the Universal Protein Resource (Uniprot) and Gene Ontology catalogs. The complete human repository of proteins from the Uniprot knowledgebase, including protein-specific accession numbers, molecular weight information, and keyword associations, was loaded into the My SQL database.

Software Implementation

The software was written in Java to facilitate platform independence. Reference and experimental data were stored in a MySQL database. The Apache POI library was used to read and write Excel files. The Apache Commons Math library was used as a standard resource to compare implemented statistical calculations and to calculate p-values from t-statistics. The standard analytical software R was also used to compare and validate implemented statistical calculations and for cluster analysis. The software was run on a standard desktop computer running Linux or Mac OS X. An auxiliary program incorporating the Python Imaging Library was used to generate heat map images. Prism (version 4.0a) was used to calculate frequency distributions for the visualization of trends following data analysis and Microsoft Excel was used to produce graphs.

Computation and Application Control Flow

Using a GUI interface, experimental data were integrated into the MySQL database after export from CPAS as Microsoft Excel files. Excel files combined MS runs from a single experiment and contained all of the information available from CPAS analyses, including columns for peptide sequence, gene name, MS run/fraction name, PeptideProphet score, protein accession number, scan number, retention time, and quantitative analysis fields. Further descriptions of these fields are available in the CPAS documentation.

Fractions named in CPAS-derived Excel files corresponded to MS runs from each excised gel slice per experiment. These fractions were defined in units of molecular weight by user input at the GUI interface. To simplify the task of user input, the software searched each Excel file and identified all fractions. The user provided the approximate maximum and minimum molecular weight restrictions for proteins identified in each MS run according to the boundaries of the gel slice from which the proteins were extracted during sample preparation.

The software queried experimental data against the human protein repository downloaded from UniProt and keyword categories defined by both UniProt and Gene Ontology catalogs. Six optional filters with user-defined parameters control the data that was used for quantitative analysis (Table 1). For each query, three reports were generated in Excel or CSV formats: a Details Report, a Keyword Overlap Report and a Keyword Overlap Table (examples are available in Supplementary Data). A large number of display options are available so that reports could be generated for readable summaries or detailed analyses.

The Details Report displays filtered peptide sequence data organized by gene, keyword and experiment. Descriptive, normality and t-statistics were calculated for the population of peptide sequences defined by each gene, keyword or experiment. To simplify troubleshooting, the Details Report included peptide sequences that failed to pass each filter, along with the parameters of the filter used to generate the report.

The Keyword Overlap Report compares genes within each keyword category and reports an overlap score based on commonality between all pairs of categories. Display options for the Keyword Overlap Report include an explicit list of the genes shared and excluded from each keyword pair and a reiteration of gene and keyword statistics from the Details Report.

The Keyword Overlap Table displays the overlap scores calculated for the Keyword Overlap Report in tabular form. Each row and column is a keyword and each table entry is the overlap score for that pair. The tabular format is analogous to mileage charts between cities in a road atlas and provides an easy visual aid for distinguishing functional protein groupings. A user-defined threshold was provided to reduce the display of overlap scores between keywords to those above a given value.

Figure 1:
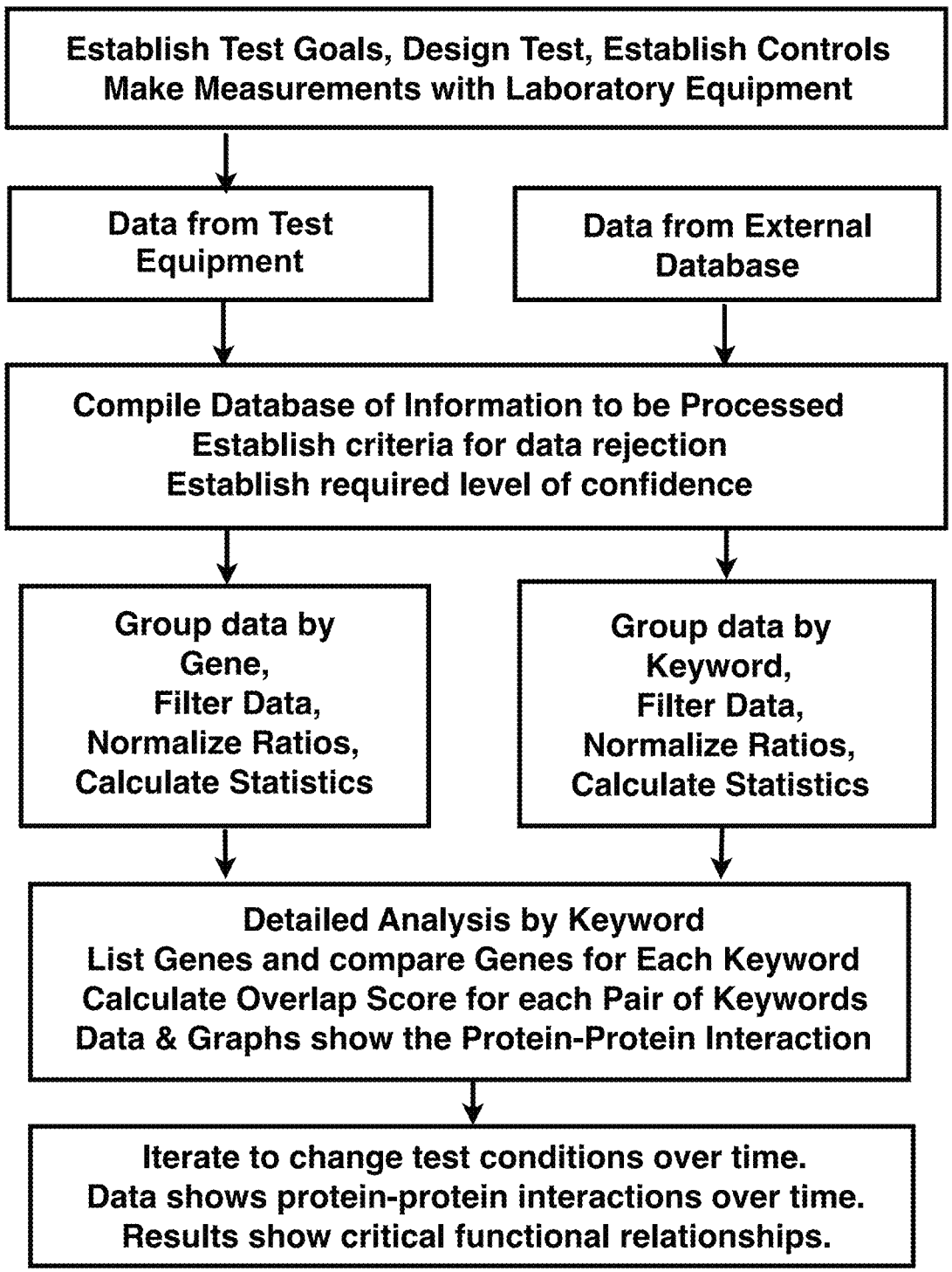
FIG. 1 is a flow diagram that depicts data processing procedures based on the invention which corrects prior errors from equipment and software and provides accurate output data for detailed analysis. The invention provides multiple screens with specific criteria for rejection of erroneous data, so that the resulting data is accurate and reliable.

The control flow for the generation of reports is summarized in FIG. 1. The Gene Section of the Details Report is generated first, beginning with a SQL query for all of the peptide sequences within an experiment. Five optional filters are embedded in the first SQL query and peptides that pass every filter are listed and organized by gene name. Peptides that fail each filter are listed in separate indexed sections. In cases where identical peptide sequences are identified within CPAS more than once, only data with the highest PeptideProphet score are retained.

For all of the peptides that pass the first five filters, fold change ratios are calculated per peptide sequence using the integrated areas of heavy and light parent ion currents. The sixth filter confirms that the number of peptide sequences that pass the first five filters is above a user-defined threshold for each gene.

Peptide sequences that pass all six filters make up the total population of peptides at the Experiment level. These peptides are used to calculate the first round of statistics, including descriptive (mean, median, standard deviation and standard error) and normality statistics (skewness, kurtotsis and D'Agostino Omnibus K2 statistic and p-value). The sample size, defined as the number of peptide sequences used to calculate statistics, is displayed for each Experiment, Keyword, and Gene. User input determines whether the Experiment-level median is used to normalize and/or log 2 transform all fold-change ratios at the Gene level. If either of these transformations are applied, Experiment-level statistics followed by gene-level statistics are recalculated.

In addition to descriptive and normality statistics, the software calculates significance statistics for each gene. The software reports t-statistics and p-values resulting from one-sample t-tests using both the Experiment-level mean and median as the value against which the mean of each Gene is tested. In addition to this formal measure of significance, the software reports the number of Experiment-level standard deviations, or standard errors, that the mean of each Gene is distanced from the Experiment-level mean or median. Although every statistic is calculated, the user may specify which, if any, are displayed in the final report.

While the failures for the peptide sequence count cutoff filter come from the program organizing the pool of peptide sequences by gene, the failure lists for the other five filters come directly from the database. There is a separate query for each filter for the set of peptide sequences from the experiment that fails a given filter's test. If there are duplicate entries for a peptide sequence in the resulting set, the one with the highest PeptideProphet score is retained. The complete set of failures forms the Failure Section of the Details Report.

Peptide sequences that pass all six optional filters are organized at the Experiment level, the Gene level, and the Keyword level. The organization of results by keyword is determined by the 13 keyword category constraints specified by the user at the GUI interface. Statistics are calculated for each keyword term that applies to each Gene out of the total 32,378 terms available. Descriptive, normality, and significance statistics are calculated from the population of peptides that are grouped within each term.

Generally, every Gene is associated with more than one keyword term. Statistics for each term are calculated from the population of peptides that are grouped within each keyword. The degree of overlap between keywords is calculated by the number of genes that are shared between terms, as shown by the following formula:

$$\frac{Gab}{Ga + Gb + Gab}$$

The terms in the above formula are defined as: $G_{ab}$ is the number of genes shared between keywords a and b, $G_a$ is the number of genes associated with keyword a, and $G_b$ is the number of genes associated with keyword b. The resulting score is a number between 0 and 1, where 1 represents complete overlap.

The Keyword Overlap Report lists all Genes that are associated with each Keyword and Genes that are shared between Keywords. To assist with analysis, the user has the option to display statistics for each Gene within each Keyword term. The Keyword Overlap Table converts a flat list of overlap scores for every pair of keywords to a matrix display.

Results

The features and advantages of the present invention should be apparent from the following description of the preferred embodiment, which illustrates, by way of example, the principles and details of a typical test procedures that were used to produce specific results.

Generation of Data With Reverse Isotopic Labeling

FIG. 2 illustrates the series of steps to generate data for LC-MS/MS analysis. To control the standardization of experimental variables, HL60 cells were differentiated in culture and split into two groups prior to treatment with LPS. The control group and LPS-treated group were lysed and enriched for phospho-protein complexes on separate affinity columns. The eluate from each column was loaded with equal total protein content and separated by gel electrophoresis. The equal loading of each gel was important to ensure accurate relative ratios between samples for quantitative analysis.

Fractions determined by molecular weight boundaries in the gel were excised, digested and labeled with 16O or 18O at peptide COOH-termini using trypsin. Although both protein digestion and peptide labeling were carried out by trypsin, the two processes were performed in series to ensure completion of each reaction. Differentially labeled samples were combined in equal volumes and submitted for LC-MS/MS analysis. The control and LPS-treated samples each provided two reverse-labeled peptide populations that were combined to form pairs from opposite labeling. This reverse-labeling strategy was intended to provide validation for peptide quantitation, independent from any bias in labeling efficiency at different substrate sequences.

Data Filtering Strategy

The CPAS platform was used to identify peptides from fragmentation spectra and calculate average parent ion intensities over the total number of scans in which they were observed. Data exported from CPAS contained over 15,000 peptide identifications per experiment. Initial inspection revealed false pair associations and unreasonably large ratios between heavy and light peptide pairs. For example, search parameters had not been modified to differentiate between terminal lysine residues that would be modified by enzymatic transfer of 18O and internal lysine residues that would not be modified.

Therefore, peptide pairs were assigned with differences of 4, 8, and 12 Da, although a difference of only 2 or 4 Da between heavy and light pairs was experimentally feasible. In addition, ratios were calculated from paired peptide elution areas that exceeded 1:100. Manual inspection of the .raw data confirmed that these values were excessive and the result of false peptide pair associations. Therefore, we implemented a set of logical rules to remove unreliable peptide data that contributed to the inaccuracy of measurements of relative protein abundance.

We began by implementing five filters based on simple arithmetic calculations that are rooted in the basic model of peptide behavior during gel electrophoresis followed by liquid chromatography and mass spectrometry. All of the filters were developed to respond to parameters that are configurable by the user, and all of the filters are ultimately optional. Two filters take into account chromatographic characteristics of peptides; "scan cutoff" limits the minimum number of scans over which a peptide must be observed to ensure a reliable elution profile, and "Light-Heavy scan cutoff" limits the minimum number of scans in which light and heavy isotope labeled peptides are not both present, thereby requiring co-elution.

Two additional filters use heavy and light peptide pairs to ensure the quality of quantitative data: "delta mass cutoff" limits the difference in mass between heavy and light labeled peptide pairs, according to the isotopes that were used during sample preparation, and "ratio cutoff" limits the numeric value of the ratio between peptide elution profile areas. The last of the first five filters, "molecular weight cutoff," imposes a limit on the percentage of error between the expected molecular weight of a protein from which a peptide was derived, as reported by UniProt, and the fraction of the gel from which the protein was excised. After the removal of peptide data that failed these filters, peptides were organized according to the Gene to which they were assigned. The sixth and final filter, "peptide sequence count cutoff," removes the genes whose number of peptide sequences is less than or equal to the cutoff value.

The final grouping of genes and peptides that remained was used for quantitative analysis. The program output was designed to report all peptide sequences that did not pass each filter according to parameters specified by the user. Whether data passes or fails a filter, no data is hidden from the user. Therefore, it is possible to compare reports using different parameter values. The threshold for each filter was manipulated during the analysis of our datasets and the results are summarized in the proceeding sections.

Filters 1 and 2: Chromatographic Elution Profile

The chromatographic elution profile of peptides provides two characteristics that can be used to enforce accurate quantitative analysis: the duration of elution and co-elution of peptide pairs. Exploratory studies have determined that increasing the smoothness of a peptide elution profile increases the accuracy of measurements of peptide abundance (Yang, Yang et al. 2010). Therefore, a threshold value defined by user input was established for the minimum number of total scans for each labeled peptide.

By requiring a minimum duration for which a peptide is observed in MS, we were able to filter out ions with very short and sporadic appearances. Maximizing the duration of peptide elution was used a proxy for continuous peptide elution, an important characteristic in peptide chromatography and one that is used by many proteomic tools, including the Trans-Proteomic Pipeline (TPP) (Li, Zhang et al. 2003). Even very low limiting thresholds for the duration of peptide elution were successful at removing input from sporadic ions (Table 2). This had the effect of reducing false pairings of ion peaks and improving the quality of data that was included in the final analysis.

The co-elution of isotope-labeled heavy and light peptides by liquid chromatography is one confirmation that they share identical peptide sequences. Co-elution and subsequent analysis in a shared set of MS scans is also a requirement for the accurate comparison of peptide pair ion abundance. To act as a true internal reference that minimizes the influence of variability in ion intensity between MS scans, peptide pairs must be present in the same MS scan. While algorithms have successfully been used to identify ion pairs within unprocessed MS spectra (Volchenboum, Kristjansdottir et al. 2009), our technique verifies peptide co-elution at the level of post-processing. This approach is not computationally intensive and allows end-user control over filter parameters. A user-defined threshold limits the number of MS scans that are not shared between peptide pairs, thereby maximizing the duration of co-elution.

There are some disadvantages to using filters at the level of post-processing data analysis. Upstream software may not provide informative quantitative parameters and limit the effectiveness of downstream filters. For example, we found that data exported from CPAS displayed identical start and end scans for every heavy and light peptide pair. The result was that the filter used to remove peptide pairs with insufficient chromatographic overlap was not effective. Any threshold value input generated identical output. Inspection of the .raw files clearly showed different start and end scans for each peptide in every pair. This highlights the utility of increased transparency in processing software and presents a case for permissive and information-rich analyses during early processing steps followed by more stringent analyses based on user-defined parameters in later steps.

Filters 3 and 4: Relative Quantitative Analysis From Labeled Pairs

Peptide pairs are defined by the difference in mass between isotopically labeled samples. The data generated for these experiments were derived from sample sets labeled with either 16O or 18O at one or both sites of the peptide COOH-terminus. Heavy and light peptide pairs were therefore defined by a 2 or 4 Da. difference in mass, depending on whether one or both oxygen atoms at the COOH-terminus were labeled. Incomplete labeling can lead to several challenges for accurate quantitation and requires the use of a specialized application for data processing (Mason, Therneau et al. 2007).

To test for incomplete labeling in these experiments, we imposed a threshold value of 2 Da. for a filter designed to exclude incorrectly paired peptides from analysis. A maximum difference of 2 Da. excluded all peptide sequences from analysis, confirming complete labeling in both experiments (Table 2). On the other hand a threshold value of 4 Da. resulted in the exclusion of several hundred peptides (Table 2). This suggested that upstream processing software did not exclude internal lysine and arginine residues from the identification of peptide pairs. While this filter is useful to define peptide pairs by the difference in mass between them, this filter can also be considered a second independent validation of chromatographic co-elution. The set difference in mass between pairs confirms that both peptides are present in the same spectrum, which is a result of chromatographic co-elution and peptide sequence identity.

The software was designed so that the user defines expected differences in mass between heavy and light peptides. To accommodate use with any labeling scheme, a list of possible values can be used to define peptide pairs at the GUI interface. Although the data used in these experiments were generated with high mass accuracy, so that an input threshold of 4.008 Da. would be appropriate, the software was also designed for use with data from instruments that provide less confidence. Therefore, any difference in mass that was within 0.1 Da. of the input value is retained. Because much of the work in quantitating peptide pairs was performed by upstream software, a strict threshold did not provide any additional benefit in this analysis.

A second filter was imposed to limit inaccuracy in quantitative analysis between peptide pairs. In our analysis we noticed that the relative areas of heavy and light peptide ions sometimes reached extreme values nearing 1:100 and 1:1000. These outliers significantly broadened the standard deviation of the relative peptide ratio mean at the Gene level, reducing confidence in the quantitative analysis. To exclude these values from the analysis, a quantitative threshold was imposed on peptide pairs that established a minimum relative ratio between peptide ion chromatogram areas. Algebraically, this also implies that those ratios must be less than the reciprocal of the threshold value, providing a limit on maximum values for fold-change ratios.

The ratio cutoff filter removed several hundred peptide sequences in our data sets that demonstrated a greater than 20-fold difference in relative ion areas. Interestingly, around half of the total peptide sequences demonstrated a greater than 2-fold difference in relative ion areas (Table 2). This filter was valuable for investigating the distribution of relative differences in peptide abundances across the entire experiment and results after exclusion of extreme pairs.

Removal of these outliers with extreme values increased the precision and accuracy of relative peptide ion quantitation and the resulting analysis at the Gene level (MacCoss and Wu 2007).

Filters 5 and 6: Gene Assignments

Peptide sequences were organized by the gene name of proteins to which they were assigned in upstream analyses. Organization by gene name provided the basis for two additional filters limiting the inclusion of peptides in quantitative analyses. The first filter took advantage of molecular weight boundaries defined by the gel slice from which a protein was excised. The filter was intended to limit analysis at the Gene level to peptides that were digested by trypsin and were not the result of protein degradation. It was also intended to prevent oversampling of contaminating proteins that were present in every gel slice.

Identified proteins were referenced against the Uniprot database and molecular weight information was matched against fraction definitions provided by the user. The filter established a percentage of error that would be tolerated for the protein molecular weight, as determined by UniProt. Peptides from proteins that were identified in appropriate fractions, with added or subtracted error, were retained. The limitation of this filter was that the molecular weight noted by UniProt pertains to the protein precursor and not to the active form of expressed proteins. Despite this limitation, a broad error allowing two times, or 100% of, the expected protein molecular weight removed over six hundred peptides from the total analysis.

A person skilled in the art would recognize that the removal of NH2-terminal protein sequences and the addition of various post-translational modifications would not be expected to affect the expected molecular weight by over 100%. Therefore, this filter was valuable for the determination of relative protein degradation and contamination per experiment.

The final filter established that every protein included in the final population was identified by a minimum number of peptide sequences. For example, the quantitative analysis of a protein from one relative peptide ratio between samples cannot be counted with confidence and that protein should be excluded. The advantage of this filter is that it can be used to limit the analysis to proteins that were sampled at high frequencies, and therefore identified and analyzed quantitatively with high confidence.

Statistics and Heuristics to Guide the Selection of Important Genes

We used descriptive statistics for a preliminary analysis of the filtered set of peptide sequence ratios. We examined the population of all peptide sequences in each experiment, for each Keyword grouping, and for each Gene grouping to get a global view of abundance distributions. The average abundance for peptide heavy and light ratios was close to equal at the Experiment level, confirming equal total protein abundance between samples. Nevertheless, each peptide ratio was normalized by the median of all labeled peptide ratios to ensure that abundance comparisons were based on a stable baseline.

We used the perspective provided by the total population of labeled peptide ratios to describe patterns and trends in the data. The standard deviation and standard error of the mean of all labeled peptide ratios at the Experiment level highlighted Genes that were very different in abundance from the majority of the population. We also incorporated a one-sample t-test that compared the mean of each Gene or Keyword grouping against the experimental mean by using the number of peptide sequences in each grouping to determine the degrees of freedom. By rapidly identifying groups that were significantly different from the experiment mean we selected for Genes and Keywords that were most affected by LPS treatment.

Significantly, this invention uses a unique approach for selecting important Genes and Keywords. By contrast, the prior methods that have been developed to determine which Genes which merit investigation do not have specified standards for selection, so that an investigator may not be able to duplicate the results of another investigator. This is because prior methods fail to hold constant the criteria for Gene selection between any two investigators. Because of this variable is not controlled, the results of laboratory tests are not consistent between investigators.

As a significant improvement, this invention implements a set of rules for statistics and heuristics that are applied uniformly to data sets to determine significance a priori for changes in abundance based on the total population in an experiment. For example, ASAPRatio uses a log-transformed fitted normal, justified by the central limit theorem for large sample sizes, and an error function to generate p-values (Li, Zhang et al. 2003). By contrast, GOMiner uses Fisher's exact test and q-values to handle small sample sizes (Zeeberg, Feng et al. 2003).

Small sample sizes are the most common condition for Gene groupings of proteomic data acquired by mass spectrometry. Accordingly, the t-test is appropriate to adjust the confidence level to reflect the sample size. The t-test has heuristic value and transparency for use as the standard metric. However, existing calculation methods merely encourage the heuristic use of statistical tests. Although the software presented here can be used heuristically, we found that by including sample sizes and normality data, the t-test can be applied appropriately for a strict and rigorous test of significance.

The t-test is widely used to show significance within data sets but relies on normality assumptions. Previous use of the t-test for data obtained by mass spectrometry is associated with several challenges. For example, implicit assumptions that support the use of the t-test for genomic microarrays do not carry over consistently to proteomic data obtained by mass spectrometry. Therefore, t-test has been often been used with caveats that strongly limit its value. To enable a rigorous use of the t-test for identifying Gene and Keyword groupings that are significantly different from the majority of the population, we implemented a set of statistics related to descriptions of normality.

Normality was described heuristically by values calculated for skewness and kurtosis within populations of peptide ratios. As a more formal test for normality, we implemented D'Agostino-Pearson Omnibus K2 scores and D'Agostino p-values (D'Agostino, Belanger et al. 1990). From these statistics, we found that the commonly used approximation of data normality by log-transformation of fold-change ratios for peptide sequence abundances is not accurate.

A second method that may have been applied to the handling of mass spectrometry data following its successful use in microarrays, is the calculation of relative abundance from the direct ratio between labeled peptides. We used our software to compare Gene level log-transformations of mean fold-change ratios calculated from peptide heavy to light ratios and the mean ratios of their reciprocals.

We also calculated a new metric for fold-change that we found to be more precise. The new metric calculates the ratio of heavy or light-labeled peptides in relation to the total area of both peptide ions over chromatographic time. For every peptide pair, the fold-change ratio is between 0 and 1. This simplifies computations and facilitates comparisons within and between peptide pairs. This metric is convenient for comparing treated and control samples because abundance ratios for each share the same denominator and are not defined by a dependent principle.

In contrast, the mean of peptide fold-change ratios and their reciprocals are independent of one another. Most importantly, calculation of the fold-change ratio by relation to a total corrects for a sloping baseline within the total data set. Sloping baselines prevent accurate comparisons between peptide ratios in a data set and severely affect the precision of every measurement. This correction is required because the precision of measurements in mass spectrometry is not directly related to the number of ions acquired or the observed ratio, as might be the case for colorimetric ratios obtained in microarray experiments (MacCoss, Wu et al. 2002). The new metric defines an internal scale from 0% to 100% that is common to every peptide ratio. Indeed, by using this new metric for fold-change, we found that standard deviations for mean peptide ratios at the Gene level were drastically reduced.

Using peptide ratios in relation to the total pair area resulted in a second improvement in data distributions. Fold-change ratios calculated from the total peptide pair area approached normality without the log-transformation that is commonly used to correct for skewness in direct ratios of peptide ion areas. For the calculation of fold-change from the direct ratio between heavy and light-labeled peptides, the left tail is truncated at 0 while the right tail can be arbitrarily long, introducing skewness. By using a ratio determined by the total paired peptide ion area, the range of values is constricted from 0 to 1. In effect, both tails are truncated thereby minimizing the standard deviation of the total population. This also has the effect of producing low kurtosis scores that increase the power of one-sample t-tests (Reineke, Baggett et al. 2003).

In the end, log-transformation of fold-change ratios at the peptide level generate populations that only appear more normal than the untransformed data. To illustrate this point, we compared skewness and kurtosis values for Log 2-transformed heavy:light ratios and heavy:total ratios in our data sets. We found that based on skewness and kurtosis alone, heavy:total ratios showed an improved distribution. By avoiding log-transformations and approaching normality with the calculation of a consistent fold-change metric, we were able to avoid the confusing circumstance of having to transform data and their statistics. For example, investigators would not have to specify that all Gene means from log-transformed peptide ratios are geometric means.

Categorical Analysis

While gene names provide a natural first grouping for peptide sequences, they have some drawbacks. Statistically, they can result in very small sample sizes. Perhaps more importantly from a biological standpoint, they are not the appropriate unit for the analysis of global changes at the cellular level. One primary example is the determination of experimental treatment effects on a network, such as a signaling pathway. In this case, the analysis of changes in abundance at the protein level and statistical methods to combine results in a meaningful way can be difficult.

Several descriptive tools have been developed to categorize lists of genes by function and report statistical scores for the enrichment of keyword categories using Gene identification alone, such as David (Huang, Sherman et al. 2007). In addition, programs such as Scaffold (Searle 2010) and Cytoscape (Shannon, Markiel et al. 2003) generate pie charts showing the distribution of keyword membership and interaction networks based on Genes identified in each experiment.

As a significant improvement to these descriptive tools, this invention includes a quantitative method for investigating the relative abundance of keywords in experimental data. Existing keyword dictionaries, included with Uniprot and Gene Ontology, provide gene names by category, including molecular function, cellular compartment, post-translational modification and associated ligand. This invention stores this information locally in a database and uses indexed tables and optimized queries, to organize protein and peptide sequence data by keyword. This invention allows efficient comparisons from the large database, so that results are obtained in an average of thirty seconds. Because each keyword captured multiple genes, groupings by keyword generated sample sizes that were more conductive to hypothesis testing.

The richness of the Uniprot and Gene Ontology keywords provides a widely accepted set of categories for classification. Groupings by keyword allow for initial comparisons between experiments. For example, instead of requiring the same protein to be sampled in each experiment, proteins within the same keyword category can be observed and grouped for a summary effect. Importantly, classification of experiment data by keyword provides insights that are not evident when the classification is by gene name. This invention allows critical protein functional relationships to become evident based on quantitative analysis of relative peptide abundance, statistical measures of significance, and categorical keyword groupings.

Keyword categorization provided a second layer of abstraction for proteomic analysis: the degree of keyword overlap within and between experiments. For any two keywords, the number of shared Genes divided by the total number of unique genes for both keywords gave a percentage overlap value. Keyword overlap provided an intuitive means for detecting networks of Genes that serve multiple functions within a cell. This novel invention is particularly useful for determination of complex patterns of protein interaction, such as prediction of multiple targets within a signaling network following pharmaceutical stimulation or inhibition.

CONCLUSION

For the preferred embodiment, the novel method is used to analyze the data produced by mass spectrometry equipment in combination with other specialized equipment, such as LC-MS/MS (liquid chromatography tandem mass spectrometry). This novel method offers unique advantages over prior analytical methods. The unique benefits are accurate protein identification, accurate measurement protein function and activity, and measurement of protein interactions between each pair of proteins in a sample. With sequential tests over time, the interactive functional relationships between proteins can be derived. The analytical results are displayed in a manner that allows disclosure of the underlying structure of the complex data.

The preferred embodiment of the method is a computer software program, written in Java, which can be used in computers using a standard operating system, such as Windows or Macintosh. The preferred embodiment is used to calculate the relative difference in protein and keyword abundance from ratios of labeled peptides between control and treated cells.

The relative abundance is calculated from the mean relative abundance of groups of peptides. Although this method could be used based on data from entire proteins, peptides are the widely-used standard experimentally observable unit for mass spectrometry investigations of proteins (Kuster, Schirle et al. 2005).

Peptides were excluded from analysis based on specified criteria to increase confidence in the quantitation of relative mean protein abundance. These specified criteria include the requirement for a minimum of 30 MS scans per peptide, a temporal overlap between MS scans of labeled peptide pairs, and a minimum of two unique peptides per protein.

To exclude quantitation from degraded protein fragments, a maximum difference of 30% was required between the expected protein molecular weight, as determined by UniProt (http://www.uniprot.org), and the molecular weight boundaries of the gel slice from which the protein was derived. Peptides with very large or very small ratios were generally indicative of false associations within CPAS and were excluded. To place greater statistical value on unique peptides within a protein, duplicate peptides were removed by selecting those with the best Peptide Prophet scores. Unequal 1:1 mixing between the control and treated samples was corrected by protein normalization using the population median.

The data from the peptide measurements are compared to detailed protein information from a widely-accepted database of protein characteristics. Test data are rejected based on a series of standard screening criteria which prevent erroneous data from being considered in final calculations. The criteria includes six fundamental standards, such as data that is not consistent with widely-accepted biochemical principles. Based on the refined measurements, the results are sorted by gene and by Keyword classification, to show fundamental relationships for each protein.

The data analysis results are unique in showing clearly relationships that were previously incomprehensible due to the complexity of the underlying data. As a result, critical decisions can be made based on the meaningful details, such as the extent of protein-protein interactions, and the effects of inhibitors on kinase activity over time. In this way, improved decisions can be made with regard to unresolved issues as to protein activity and function, including signaling networks and subtle functions of the immune system.

Based on separate multiple measurements over time, the method provides the factual foundation that would support inference of causation based on the functional variation of peptide activity for any combination or permutation of any two pairs of peptides over time. The novel features of the invention is error correction features, which reject erroneous measurements or calculations from the output of the laboratory equipment.

This invention interprets and screens the machine outputs, so that any variation or deviation from established criteria results in rejection of the sample measurement based on a sequential series of screening tests, in exactly the same manner for each peptide in the sample. Therefore, this novel method forces each measured sample to meet specific criteria as to verification of identification, accuracy of measurement for the amount of activity, and the effect of the inhibitor or other compound on the activity of the peptide. The accuracy of each measurement is verified through separate controls internal to each sample that is exactly matched as to all possible variables.

This invention allows custom modifications by a person skilled in the art. For example, in addition to the sets of keywords provided by Uniprot and Gene Ontology, user-defined sets of keywords can be added to the database. Also, a person skilled in the art could add widely accepted tests for excluding outliers as part of the filtering process for the raw input and nonparametric statistics to give more avenues for investigating the data, especially when small sample sizes are under consideration.

This invention provides a standardized means of proteomic analysis. An accurate description of test conditions and calculation methods is necessary to allow accurate comparison between tests from different investigators. This invention describes important cellular changes by the interplay of patterns provided in complete analyses of proteomic data.

Proteomic experiments provide global observations that may isolate previously unknown proteins by their functional importance. However, by selectively reporting changes in a small group of proteins of interest, proteomics studies often fail to describe the accurate intracellular environment from which measurements were made. To assure accurate comparison of test results, a standard calculation method is required (Pedrioli, Eng et al. 2004).

This invention provides a major improvement for calculation of mass spectrometry test results. With this new method, an investigator can modify specific analytical criteria with a clear description, with specificity, as to each calculation element that was used for each test. This full description of test conditions allows a clear comparison of test results between investigators.

THE PRIMARY ADVANTAGES OF THE NEW METHOD

Mass spectrometry is the most common instrument used for protein biomarker discovery in complex samples. Existing software is successful at providing statistical evidence that a given protein has been correctly identified from measurements of molecular mass and charge. Moving past a simple description, quantitative mass spectrometry is concerned with determining the difference in abundance for a given protein in a comparison of two samples. Current proteomics research goes beyond mere correct protein identification, to detailed analysis of significant changes in protein abundance. This requires robust, accurate, undistorted measurement of peptide characteristics across a wide variety of experimental settings and conditions. For the data to be meaningful, these measures have to be examined in a biological context.

The critical need for this sophisticated software is shown by recent reports that demonstrate inconsistent results and inaccurate measurements from current mass spectrometry equipment and software, despite careful laboratory controls. Although various types of mass spectrometry software have been used in proteomics for over a decade, the current emphasis on protein activity within a biological context results in the requirement for significant software improvements.

With the new method, mass spectrometry may be used to describe the significant functional relationships and activity for sampled proteins within the cell. With improved software, the horizons of systems biology can be expanded to include detailed information on protein signaling networks, to complement the expanding knowledge of genomics. This method demonstrates unique advantages toward this goal, such as: (a) accurate calculation of the relative abundance of sampled proteins and functional keyword categories, (b) multiple screening to reject errors, sorting by specified criteria, and specification of the relevant protein activity, (c) display of significant relationships between sampled proteins and keywords, highlighting quantitative activity signatures specific to the experiment.

As a significant innovation, this new method addresses important problems in proteomic analysis, with significant improvements in accuracy, reliability, and information content. This new method provides detailed calculations and functional annotations, to replace prior manual calculations, and supports new avenues of investigation due to the ability to highlight functional trends in complex data.

This new method was developed to correct the errors found in current mass spectrometry software, such as lack of capability for accurate replication of the results of a published experiment, due to failure to adjust quantitation to the characteristics of different equipment and a lack of consistent analytical methods for independent scientists to evaluate the data.

This new method corrects the errors of inaccurate measurements with limited information content, significant identification errors, and high data dispersion. With prior methods, the identification is merely nominal, based on database association of the protein and gene name, without display of critical network relationships or the effects of changed test conditions.

Several key features of this new method are not available with other methods. One of the key features is heuristic filtering of data to accommodate the behavior of various mass spectrometry instruments and the inclusion of the investigator's judgment. The new method allows adjustments for machine-learning algorithms to optimize analytical settings for each particular experiment, thereby automating standardization procedures.

Another key advantage is that this new method allows use of a wide array of statistical analysis methods, including classical significance tests, to find meaningful changes in protein abundance based on the complete sampled population. Useful graphic displays of the data are included in the method, such as cluster analysis and heat maps, to demonstrate significant relationships within the data, and to highlight the correlation of protein activities in response to specific stimuli.

As a major advantage, this new method allows organization of quantitative data by recognized keyword categories to reveal changes in the abundance of functional groups and their degree of overlap. A keyword is a descriptive classification that is widely recognized and understood in the biological research field, as a summary of essential characteristics. The result is a cohesive and functional signature, as opposed to disparate biomarkers with unclear relationships or biological context. These aspects of the software will be developed further to include the generation of self-organizing maps and Bayesian or neural network models, which will identify new functionally significant relationships within the data.

The new method allows the investigator to continue to use the functional terminology of widely used existing databases, such as UniProt and Gene Ontology, to organize the observed data into units of statistical analysis based on biologically meaningful keywords. This gives researchers an easy way to look at the question of abundance in terms of cellular localization, function and disease instead of as lists of unrelated proteins devoid of a larger context. Using this as a starting point, the new method can also quantitatively describe relationships between categories, which may prove relevant for investigating non-specific interactions from therapeutic treatments.

Those skilled in the art will recognize, or be able to ascertain using no more than routine experimentation, many equivalents to the specific embodiments of the invention described herein. Such equivalents are intended to be encompassed by the following claims.

What is claimed is:

1. A method comprising:
preparing a biological sample containing proteins;
subjecting the sample to analysis by a mass spectrometer;
receiving a raw data set from the mass spectrometer, the raw data set representing ion spectra corresponding to peptides or peptide fragments within the sample;
identifying peptides, proteins, or gene names from the raw data set by use of a data processor and processing instructions executing thereon, the identifying including transforming the raw data set to a structured data set formatted for pattern recognition using the data processor, the transforming including filtering the raw data set based on chromatographic and elution characteristics of the sample, the identifying further including comparing portions of the structured data set to a protein or gene index thereby identifying the peptides, proteins, or gene names corresponding to the sample;
implementing a set of logical rules to selectively filter the peptides, proteins, or gene names identified from the structured data set using filter parameters to isolate filtered peptides, proteins, or gene names, the selective filtering including filtering the peptides, proteins, or gene names according to a minimum relative ratio between peptide ion chromatogram areas;
correlating the filtered peptides, proteins, or gene names with corresponding keywords by use of the data processor and the processing instructions executing thereon;
calculating peptide abundance from the filtered peptides, proteins, or gene names by use of the data processor and the processing instructions executing thereon;
calculating protein abundance from the filtered peptides, proteins, or gene names by use of the data processor and the processing instructions executing thereon;
calculating keyword abundance from the filtered peptides, proteins, or gene names, and correlated keywords by use of the data processor and the processing instructions executing thereon; and
generating, by use of the data processor and the processing instructions executing thereon, a keyword overlap score based on a correlation of the gene names corresponding to the filtered peptides and proteins and the keywords associated with the gene names corresponding to the filtered peptides and proteins.

2. The method of claim 1 further including generating, by use of the data processor and the processing instructions executing thereon, data and graphic pattern representations of peptide functions and interactions based on the calculated peptide abundance, the keyword abundance, and the keyword overlap score for the filtered peptides.

3. The method of claim 1, wherein filtering the raw data set further comprises: filtering the raw data set using heuristic filtering of the raw data to accommodate the behavior of various different mass spectrometers.

4. A system comprising:
a mass spectrometer for analysis of a biological sample containing proteins; and a data processor with data processing instructions executing thereon, the data processing instructions being configured to cause the data processor to:
receive a raw data set from the mass spectrometer, the raw data set representing ion spectra corresponding to peptides or peptide fragments within the sample;
identify peptides, proteins, or gene names from the raw data set by use of the data processor and the processing instructions executing thereon, the identifying including transforming the raw data set to a structured data set formatted for pattern recognition using the data processor, the transforming including filtering the raw data set based on chromatographic and elution characteristics of the sample, the identifying further including comparing portions of the structured data set to a protein or gene index thereby identifying the peptides, proteins, or gene names corresponding to the sample;
implement a set of logical rules to selectively filter the peptides, proteins, or gene names identified from the structured data set using filter parameters to isolate filtered peptides, proteins, or gene names, the selective filtering including filtering the peptides, proteins, or gene names according to a minimum relative ratio between peptide ion chromatogram areas;
correlate the filtered peptides, proteins, or gene names with corresponding keywords by use of the data processor and the processing instructions executing thereon;
calculate peptide abundance from the filtered peptides, proteins, or gene names by use of the data processor and the processing instructions executing thereon;
calculate protein abundance from the filtered peptides, proteins, or gene names by use of the data processor and the processing instructions executing thereon;
calculate keyword abundance from the filtered peptides, proteins, or gene names, and correlated keywords by use of the data processor and the processing instructions executing thereon; and
generate, by use of the data processor and the processing instructions executing thereon, a keyword overlap score based on a correlation of the gene names corresponding to the filtered peptides and proteins and the keywords associated with the gene names corresponding to the filtered peptides and proteins.

5. The system of claim 4 wherein the data processing instructions being configured to cause the data processor to generate data and graphic pattern representations of peptide functions and interactions based on the calculated peptide abundance, the keyword abundance, and the keyword overlap score for the filtered peptides.

6. The system of claim 4 wherein the data processing instructions being configured to cause the data processor to filter the raw data set using heuristic filtering of the raw data to accommodate the behavior of various different mass spectrometers.

* * * * *